(12) United States Patent
Yamaoka et al.

(10) Patent No.: US 10,574,976 B2
(45) Date of Patent: Feb. 25, 2020

(54) MEDICAL STEREOSCOPIC OBSERVATION APPARATUS, MEDICAL STEREOSCOPIC OBSERVATION METHOD, AND PROGRAM

(71) Applicant: SONY OLYMPUS MEDICAL SOLUTIONS INC., Tokyo (JP)

(72) Inventors: Nobusuke Yamaoka, Chiba (JP); Aki Mizukami, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 423 days.

(21) Appl. No.: 14/961,039

(22) Filed: Dec. 7, 2015

(65) Prior Publication Data

US 2016/0165222 A1 Jun. 9, 2016

(30) Foreign Application Priority Data

Dec. 8, 2014 (JP) ................. 2014-247651

(51) Int. Cl.
| | |
|---|---|
| *H04N 13/359* | (2018.01) |
| *A61B 90/20* | (2016.01) |
| *H04N 13/144* | (2018.01) |
| *A61B 5/00* | (2006.01) |
| *A61B 90/00* | (2016.01) |

(52) U.S. Cl.
CPC ........... *H04N 13/359* (2018.05); *A61B 90/20* (2016.02); *H04N 13/144* (2018.05); *A61B 5/0077* (2013.01); *A61B 2090/371* (2016.02); *A61B 2576/00* (2013.01)

(58) Field of Classification Search
CPC ................................................ H04N 13/0454
USPC ........................................................ 348/42
See application file for complete search history.

(56) References Cited

U.S. PATENT DOCUMENTS

| | | | | |
|---|---|---|---|---|
| 6,215,590 | B1* | 4/2001 | Okano | G02B 27/2264 |
| | | | | 359/464 |
| 2007/0126863 | A1* | 6/2007 | Prechtl | H04N 5/232 |
| | | | | 348/43 |
| 2009/0046146 | A1* | 2/2009 | Hoyt | A61B 90/35 |
| | | | | 348/143 |
| 2010/0246679 | A1* | 9/2010 | Dey | H04N 19/61 |
| | | | | 375/240.16 |
| 2013/0271608 | A1* | 10/2013 | Hiei | B60R 1/00 |
| | | | | 348/148 |

FOREIGN PATENT DOCUMENTS

| | | | | |
|---|---|---|---|---|
| JP | 06-261341 | | 9/1994 | |
| JP | H6-261341 | * | 9/1994 | ............. H04N 13/00 |

* cited by examiner

*Primary Examiner* — Joseph G Ustaris
*Assistant Examiner* — Amir Shahnami
(74) *Attorney, Agent, or Firm* — Xsensus LLP

(57) ABSTRACT

A medical stereoscopic observation apparatus having circuitry that acquires a status signal according to a status of image processing from each image processing circuit of a plurality of image processing circuits that perform the image processing on input image data through a selected image processing unit among a plurality of image processing units in the respective image processing circuit and generates output image data to be output as a right eye image or a left eye image, and causes a second image processing circuit different from a first image processing circuit to switch the selected image processing unit to match the selected image processing unit of the first image processing circuit, according to the status signal acquired from the first image processing circuit among the image processing circuits of the plurality of image processing circuits.

13 Claims, 12 Drawing Sheets

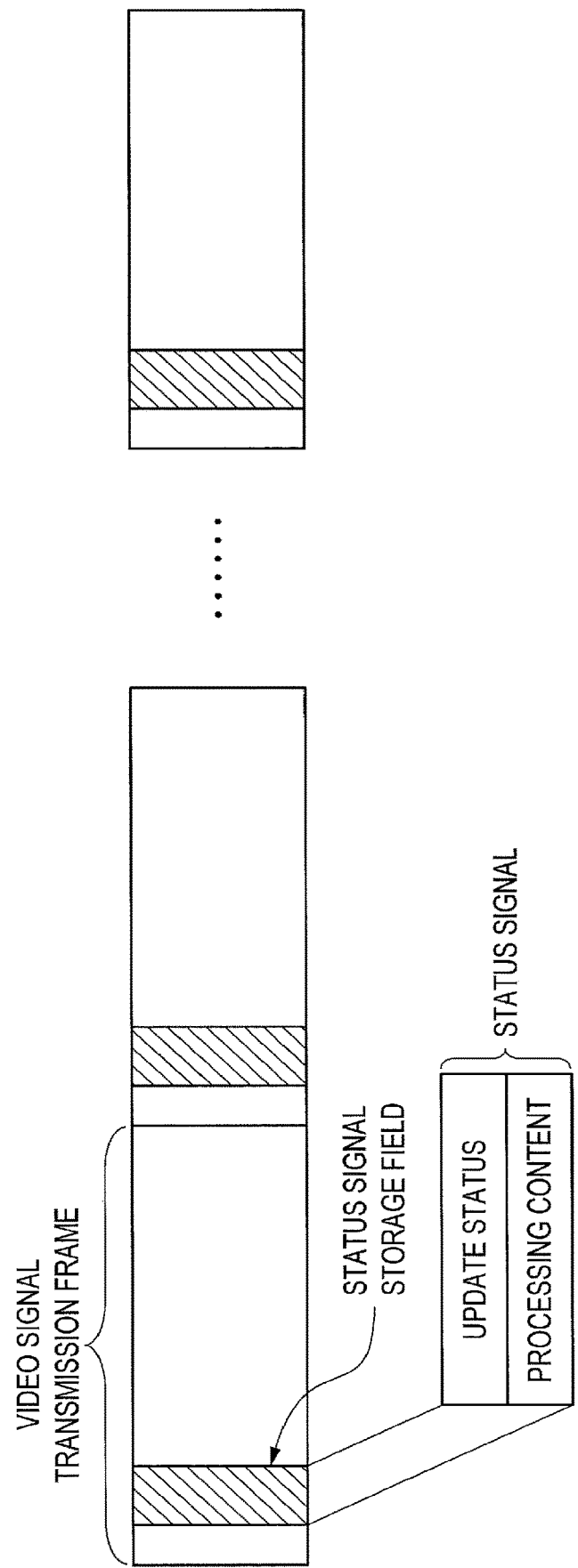

FIG. 6

| No. | LEFT INPUT | RIGHT INPUT | CONTROL FEEDBACK | LEFT OUTPUT | RIGHT OUTPUT | DEFAULT SETTING |
|---|---|---|---|---|---|---|
| 1 | HIGH FUNCTION PROCESSING IMAGE | HIGH FUNCTION PROCESSING IMAGE | AUTONOMOUS SELECTION | OWN SYSTEM SELECTION | OWN SYSTEM SELECTION | ○ |
| 2 | HIGH FUNCTION PROCESSING IMAGE | LOW FUNCTION PROCESSING IMAGE | LOW FUNCTION PROCESSING SELECTION | OWN SYSTEM SELECTION | OWN SYSTEM SELECTION | |
| 3 | HIGH FUNCTION PROCESSING IMAGE | PATTERN GENERATION IMAGE | AUTONOMOUS SELECTION | OWN SYSTEM SELECTION | OTHER SYSTEM SELECTION | |
| 4 | LOW FUNCTION PROCESSING IMAGE | HIGH FUNCTION PROCESSING IMAGE | LOW FUNCTION PROCESSING SELECTION | OWN SYSTEM SELECTION | OWN SYSTEM SELECTION | |
| 5 | LOW FUNCTION PROCESSING IMAGE | LOW FUNCTION PROCESSING IMAGE | LOW FUNCTION PROCESSING SELECTION | OWN SYSTEM SELECTION | OWN SYSTEM SELECTION | |
| 6 | LOW FUNCTION PROCESSING IMAGE | PATTERN GENERATION IMAGE | AUTONOMOUS SELECTION | OWN SYSTEM SELECTION | OTHER SYSTEM SELECTION | |
| 7 | PATTERN GENERATION IMAGE | HIGH FUNCTION PROCESSING IMAGE | AUTONOMOUS SELECTION | OTHER SYSTEM SELECTION | OWN SYSTEM SELECTION | |
| 8 | PATTERN GENERATION IMAGE | LOW FUNCTION PROCESSING IMAGE | AUTONOMOUS SELECTION | OTHER SYSTEM SELECTION | OWN SYSTEM SELECTION | |
| 9 | PATTERN GENERATION IMAGE | PATTERN GENERATION IMAGE | AUTONOMOUS SELECTION | OWN SYSTEM SELECTION | OWN SYSTEM SELECTION | |

FIG. 7

| | | d22 | | | | d20 |
|---|---|---|---|---|---|---|
| d21 | d221 | d222 | d223 | d23 | d24 | d25 |
| No. | INPUT UPDATE STATUS | LOW FUNCTION PROCESS OUTPUT UPDATE STATUS | HIGH FUNCTION PROCESS OUTPUT UPDATE STATUS | FEEDBACK INPUT | OUTPUT SELECTION | DEFAULT SETTING |
| 1 | NOT UPDATED | Don't care | Don't care | Don't care | PATTERN GENERATION IMAGE SELECTION | |
| 2 | UPDATED | OK | OK | AUTONOMOUS SELECTION | HIGH FUNCTION PROCESSING IMAGE SELECTION | ○ |
| 3 | UPDATED | OK | OK | LOW FUNCTION PROCESSING IMAGE SELECTION | LOW FUNCTION PROCESSING IMAGE SELECTION | |
| 4 | UPDATED | OK | NG | AUTONOMOUS SELECTION | LOW FUNCTION PROCESSING IMAGE SELECTION | |
| 5 | UPDATED | OK | NG | LOW FUNCTION PROCESSING IMAGE SELECTION | LOW FUNCTION PROCESSING IMAGE SELECTION | |
| 6 | UPDATED | NG | OK | AUTONOMOUS SELECTION | HIGH FUNCTION PROCESSING IMAGE SELECTION | |
| 7 | UPDATED | NG | OK | LOW FUNCTION PROCESSING IMAGE SELECTION | PATTERN GENERATION IMAGE SELECTION | |
| 8 | UPDATED | NG | NG | AUTONOMOUS SELECTION | PATTERN GENERATION IMAGE SELECTION | |
| 9 | UPDATED | NG | NG | LOW FUNCTION PROCESSING IMAGE SELECTION | PATTERN GENERATION IMAGE SELECTION | |

MEDICAL STEREOSCOPIC OBSERVATION APPARATUS, MEDICAL STEREOSCOPIC OBSERVATION METHOD, AND PROGRAM

CROSS REFERENCE TO RELATED APPLICATIONS

This application claims the benefit of Japanese Priority Patent Application JP 2014-247651 filed Dec. 8, 2014, the entire contents of which are incorporated herein by reference.

BACKGROUND

The present disclosure relates to a medical stereoscopic observation apparatus, a medical stereoscopic observation method, and a program.

In recent years, with the development of surgical techniques and surgical instruments, an operation of performing various kinds of treatments while observing an affected area through a medical observation apparatus such as an operation microscope or an endoscope (so-called microsurgery) has been frequently performed. The medical observation apparatus is not limited to an apparatus capable of optically observing an affected area, and there is an apparatus that causes an image of an affected area imaged by an imaging section (camera) to be displayed on a display unit such as a monitor as an electronic image as well.

When the image of the affected area imaged by the imaging section of the observation apparatus is displayed on the display unit, the image is mostly displayed as a planar two-dimensional (2D) image. However, since a 2D image lacks a sense of perspective, and thus it is difficult to understand a relative distance between an affected area and a treatment tool, in recent years, a technique of causing an image of an imaged affected area to be displayed as a three-dimensional (3D) image has also been developed. As described above, in an observation apparatus (which is hereinafter also referred to as a "stereoscopic observation apparatus") that causes an image of an imaged affected area to be displayed as a 3D image, for example, different viewpoint images are observed by the left and right eyes, and thus the user observes an image of an affected area as a stereoscopic 3D image.

SUMMARY

Meanwhile, in the stereoscopic observation apparatus, an abnormality may occur in one of image processing units that output viewpoint images due to a malfunction or the like. In this case, it may be difficult to display a target as a 3D image, and flickering may unfortunately occur.

For this reason, a technique of suppressing the occurrence of flickering when an abnormality occurs in one of image processing units that output viewpoint images is disclosed in JP H6-261341A. In other words, in the technique disclosed in JP H6-261341A, a switching unit is installed at a stage after the image processing units that output viewpoint images, and the switching unit switches viewpoint images to be observed by the left and right eyes based on the presence or absence of an output of viewpoint images from the image processing units, and thus the occurrence of flickering is suppressed.

Meanwhile, in the observation apparatus that causes an image of an affected area imaged by the imaging section or the like to be displayed as an electronic image, when an abnormality occurs in one of the image processing units that output viewpoint images, it is possible to observe images continuously by switching the image processing unit to an alternative unit. For this reason, there is a demand for a technique capable of applying such a mechanism even to the stereoscopic observation apparatus.

However, the image processing units before and after the switching are not necessarily configured to output the same viewpoint image. For this reason, in the stereoscopic observation apparatus, when any one of the image processing units that output viewpoint images is switched, there are cases in which the viewpoint images observed by the left and right eyes do not match, and the 3D image is not properly observed.

In this regard, it is desirable to provide a medical stereoscopic observation apparatus, a medical stereoscopic observation method, and a program, which are capable of performing control such that viewpoint images observed by the left and right eyes match in a more appropriate form even when an abnormality occurs in one of image processing units that output a plurality of viewpoint images.

According to an embodiment of the present disclosure, there is provided a medical stereoscopic observation apparatus, including: an acquiring unit configured to acquire a status signal according to a status of image processing from each of image processing sections of a plurality of systems that perform the image processing on input image data through a selected image processing unit among a plurality of image processing units and generate output image data to be output as a right eye image or a left eye image; and a control unit configured to cause a second image processing section different from a first image processing section to switch the selected image processing unit according to the status signal acquired from the first image processing section among the image processing sections of the plurality of systems.

According to an embodiment of the present disclosure, there is provided a medical stereoscopic observation method, including: acquiring a status signal according to a status of image processing from each of image processing sections of a plurality of systems that perform the image processing on input image data through a selected image processing unit among a plurality of image processing units and generate output image data to be output as a right eye image or a left eye image; and causing a second image processing section different from a first image processing section to switch the selected image processing unit according to the status signal acquired from the first image processing section among the image processing sections of the plurality of systems through a processor.

According an embodiment of the present disclosure, there is provided a program causing a computer to execute: acquiring a status signal according to a status of image processing from each of image processing sections of a plurality of systems that perform the image processing on input image data through a selected image processing unit among a plurality of image processing units and generate output image data to be output as a right eye image or a left eye image; and causing a second image processing section different from a first image processing section to switch the selected image processing unit according to the status signal acquired from the first image processing section among the image processing sections of the plurality of systems.

As described above, according to an embodiment of the present disclosure, a medical stereoscopic observation apparatus, a medical stereoscopic observation method, and a program, which are capable of performing control such that viewpoint images observed by the left and right eyes match in a more appropriate form even when an abnormality occurs in one of image processing units that output a plurality of viewpoint images are provided.

Note that the effects described above are not necessarily limited, and along with or instead of the effects, any effect that is desired to be introduced in the present specification or other effects that can be expected from the present specification may be exhibited.

BRIEF DESCRIPTION OF THE DRAWINGS

FIG. 5 is a diagram illustrating an exemplary schematic data structure of a video signal transmission frame in an image processing apparatus according to the same embodiment;

FIG. 6 illustrates an exemplary control table for implementing control according to various kinds of statuses through a control unit of an image selecting unit;

FIG. 7 illustrates an exemplary control table for implementing control according to various kinds of statuses through a control unit of an image processing section;

DETAILED DESCRIPTION OF THE EMBODIMENT(S)

Figure 1:
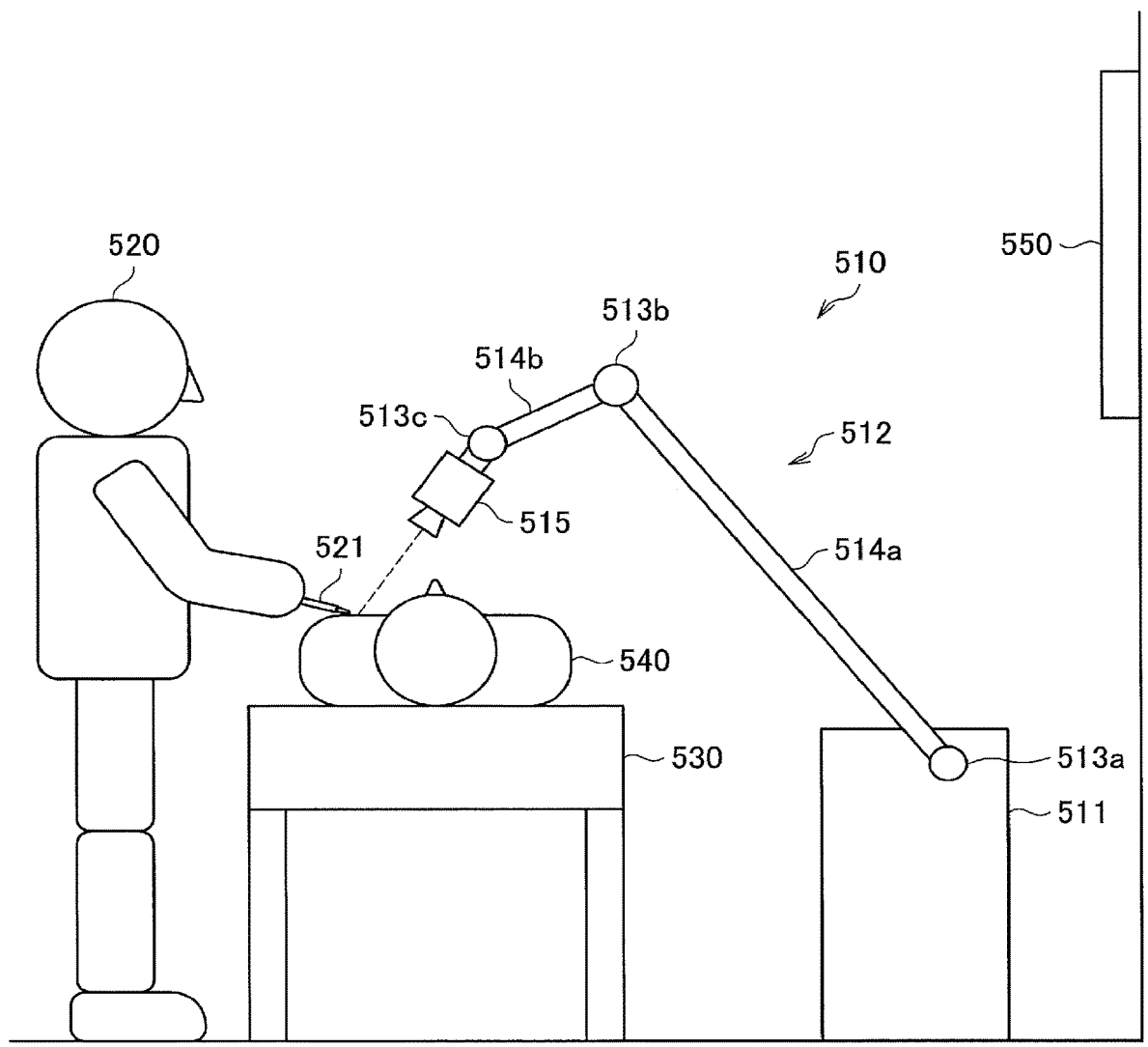
FIG. 1 is an explanatory diagram for describing an application example of a medical stereoscopic observation apparatus according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will proceed in the following order.

1. Review of Medical Stereoscopic Observation Apparatus
2. Embodiment of Present Disclosure
2.1. External Appearance of Medical Stereoscopic Observation Apparatus
2.2. Functional Configuration of Image Processing Apparatus
2.3. Details of Switching Control
2.3.1. Switching Control in Image Selecting Unit
2.3.2. Switching Control in Image Processing Section
2.3.3. First Specific Example of Switching Control
2.3.4. Second Specific Example of Switching Control
2.4. Process
2.5. Modified Examples
2.5.1. First Modified Example: Status Notification at Time of Switching Control
2.5.2. Second Modified Example: Exemplary Configuration When Image Processing is Divided into Plurality of Steps and Performed
3. Hardware Configuration
4. Conclusion <1. Review of Medical Stereoscopic Observation Apparatus>

First, in order to further clarify the present disclosure, an application example of a medical stereoscopic observation apparatus according to an embodiment of the present disclosure will be described, and then a disadvantage of the medical stereoscopic observation apparatus will be described.

An example in which an operation video microscope apparatus with an arm is used as a medical stereoscopic observation apparatus will be described as an application example in which a medical stereoscopic observation apparatus according to an embodiment of the present disclosure is used with reference to FIG. 1. FIG. 1 is an explanatory diagram for describing an application example of a medical stereoscopic observation apparatus according to an embodiment of the present disclosure.

FIG. 1 schematically illustrates an exemplary medical procedure using an operation video microscope apparatus according to the present embodiment. Specifically, FIG. 1 illustrates an example in which a doctor serving as a practitioner (user) 520 performs surgery on a medical procedure target (patient) 540 on a medical procedure table 530, for example, using surgical instruments 521 such as a scalpel, tweezers, and forceps. In the following description, the medical procedure refers to a general concept including various kinds of medical treatments that the doctor serving as the user 520 performs on the patient of the medical procedure target 540 such as surgery or an examination. The example of FIG. 1 illustrates surgery as an example of the medical procedure, but the medical procedure using the operation video microscope apparatus 510 is not limited to surgery and may be various kinds of other medical procedures such as an examination using an endoscope.

The operation video microscope apparatus 510 according to the present embodiment is installed at the side of the medical procedure table 530. The operation video microscope apparatus 510 includes a base unit 511 serving as a base, an arm unit 512 extending from the base unit 511 and an imaging unit 515 connected to the front edge of the arm unit 512 as a front edge unit. The arm unit 512 includes a plurality of joint units 513a, 513b, 513c, a plurality of links 514a and 514b connected by the joint units 513a and 513b, and an imaging unit 515 installed at the front edge of the arm unit 512. In the example illustrated in FIG. 1, for the sake of simplification, the arm unit 512 includes the 3 joint units 513a to 513c and the 2 links 514a and 514b, but practically, for example, the number and the shape of the joint units 513a to 513c and the links 514a and 514b and a direction of the driving shaft of the joint units 513a to 513c may be appropriately set to express a desired degree of freedom in view of a degree of freedom of the position and posture of the arm unit 512 and the imaging unit 515.

The joint units 513a to 513c have a function of connecting the links 514a and 514b to be rotatable, and as the joint units 513a to 513c are rotationally driven, driving of the arm unit 512 is controlled. Here, in the following description, the position of each component of the operation video microscope apparatus 510 is the position (coordinates) in a space specified for driving control, and the posture of each component is a direction (angle) to an arbitrary axis in a space specified for driving control. Further, in the following description, driving (or driving control) of the arm unit 512 refers to changing (controlling a change of) the position and posture of each component of the arm unit 512 by performing driving (or driving control) of the joint units 513a to 513c and driving (or driving control) of the joint units 513a to 513c.

The imaging unit 515 is connected to the front edge of the arm unit 512 as the front edge unit. The imaging unit 515 is a unit that acquires an image of an imaging target, for example, such as a camera capable of imaging a moving image or a still image. As illustrated in FIG. 1, postures or positions of the arm unit 512 and the imaging unit 515 are controlled by the operation video microscope apparatus 510 such that the imaging unit 515 installed at the front edge of the arm unit 512 images a state of a medical procedure part of the medical procedure target 540. A configuration of the imaging unit 515 connected to the front edge of the arm unit 512 as the front edge unit is not particularly limited, but for example, the imaging unit 515 may be configured as an endoscope or a microscope. The imaging unit 515 may be configured to be removably attached to the arm unit 512. Through this configuration, for example, the imaging unit 515 according to a use purpose may be appropriately connected to the front edge of the arm unit 512 as the front edge unit. This description will proceed focusing on the example in which the imaging unit 515 is applied as the front edge unit, but it is needless to say that the front edge unit connected to the front edge of the arm unit 512 is not necessarily limited to the imaging unit 515.

A display device 550 such as a monitor or a display is installed at a position facing the user 520. The image of the medical procedure part imaged by the imaging unit 515 is displayed on a display screen of the display device 550 as an electronic image. The user 520 performs various kinds of treatments while viewing the electronic image of the medical procedure part displayed on the display screen of the display device 550.

As described above, in the present embodiment, in the medical field, a technique of performing surgery while imaging a medical procedure part through the operation video microscope apparatus 510 is proposed.

Particularly, the operation video microscope apparatus 510 (that is, the medical stereoscopic observation apparatus) according to an embodiment of the present disclosure is configured to be able to acquire image data for displaying an imaging target as a 3D image.

As a specific example, in the operation video microscope apparatus 510, a stereo camera including imaging sections (for example, camera units) of two systems is installed as the imaging unit 515, and images (that is, viewpoint images) having a plurality of different viewpoints are acquired through the imaging sections.

For example, each of a plurality of viewpoint images acquired by the imaging unit 515 undergoes various kinds of image processing performed by an image processing apparatus installed inside or outside the operation video microscope apparatus 510 and then is displayed on the display device 550 as a left eye image and a right eye image.

As a mechanism of causing the images displayed on the display device 550 as the left eye image and the right eye image to be observed as a 3D image by the user 520, various schemes have been proposed. As a specific example, there is a scheme of causing different viewpoint images (that is, the left eye image and the right eye image) to be observed by the left and right eyes using dedicated glasses. Further, in recent years, a glasses-free 3D video technique of causing a 3D image to be observed without using dedicated glasses has also been proposed.

Meanwhile, in the operation video microscope apparatus (that is, the medical stereoscopic observation apparatus) capable of observing a 3D image based on a plurality of different viewpoint images as in the operation video microscope apparatus 510 according to an embodiment of the present disclosure, there are cases in which an abnormality occurs in one of the image processing units corresponding to the viewpoint images due to a malfunction or the like. In this case, it may be difficult to cause an imaging target to be displayed on the display device 550 as a 3D image, and flickering may unfortunately occur in the display device 550.

In light of this situation, in order to suppress the occurrence of flickering with a malfunction of the image processing unit, a technique of switching viewpoint images to be output as the left eye image and the right eye image according to the presence or absence of an output from the image processing unit corresponding to the viewpoint images has been proposed. In this technique, a switching unit installed at a stage subsequent to the image processing units corresponding to the viewpoint images detects the presence or absence of an output of the viewpoint images from the image processing units. Then, when an output of the image processing unit corresponding to one viewpoint image is stopped due to a malfunction or the like, the switching unit outputs the output of the image processing unit corresponding to the other viewpoint image as the left eye image and the right eye image. Through this configuration, when an abnormality occurs in only one of the image processing units corresponding to the viewpoint images due to a malfunction or the like, it is possible to display an imaging target as a 2D image and suppress the occurrence of the flickering.

Meanwhile, in the medical operation video microscope apparatus that causes an image acquired by the imaging unit to be displayed as an electronic image as in the operation video microscope apparatus 510 according to an embodiment of the present disclosure, there are cases in which it is difficult to observe an image when an abnormality occurs in a CPU or an image processing apparatus. Particularly, in the medical field, if it is difficult to observe an image of a surgical field during surgery, there are cases in which it is difficult to continue the surgery, and it is difficult to suspend the surgery as well. For this reason, there is a medical operation video microscope apparatus equipped with a mechanism enabling an image acquired by an imaging unit to be observed even when an abnormality occurs in a CPU or an image processing apparatus.

As a specific example, there is an operation video microscope apparatus including a plurality of units (for example, image processing units) that cause an image imaged by an imaging unit to be displayed as an electronic image. In this operation video microscope apparatus, when an abnormality occurs in one image processing unit, it is possible to observe an image continuously by switching to the other image processing unit (that is, an alternative unit).

Here, in the operation video microscope apparatus (that is, the medical stereoscopic observation apparatus) capable of observing a 3D image based on a plurality of different viewpoint images, a mechanism controlled such that the left eye image matches the right eye image is necessary. Specifically, in the medical stereoscopic observation apparatus, when different image processing from that for a viewpoint image displayed as the right eye image is performed on a viewpoint image displayed as the left eye image, there are cases in which the left eye image does not match the right eye image, and thus a 3D image is not properly observed.

On the other hand, in the case of the image processing unit that performs image processing on the viewpoint images, units that perform the same image processing are not necessarily installed as the image processing units before and after the switching. As a specific example, among the image processing units installed as a switching destination when a malfunction occurs, there is an image processing unit with a simple configuration in which an image imaged by the imaging unit is simply displayed as an electronic image without undergoing complicated image processing.

Further, as described above, the image processing unit that performs image processing on the viewpoint image displayed as the right eye image and the image processing unit that performs image processing on the viewpoint image displayed as the left eye image do not necessarily malfunction at the same time. In other words, timings at which the image processing units that perform image processing on the viewpoint images are switched due to a malfunction are not necessarily identical to one another.

For this reason, in the operation video microscope apparatus (that is, the medical stereoscopic observation apparatus) capable of observing a 3D image, for example, when the image processing unit is switched for one of a plurality of viewpoint images due to a malfunction or the like, the left eye image and the right eye image to be observed are unlikely to match. In this situation, the output from the image processing units corresponding to the viewpoint images is not necessarily suspended. Thus, even when the image processing unit corresponding to any one viewpoint image is switched, it is difficult for the switching unit positioned at a subsequent stage to detect the switching based on only the presence or absence of the output from the image processing units corresponding to the viewpoint images and cause the left eye image to match the right eye image.

In this regard, the medical stereoscopic observation apparatus according to an embodiment of the present disclosure provides a mechanism that performs control such that the left eye image matches the right eye image in a more appropriate form even when a malfunction occurs in one of the image processing units that perform image processing on a plurality of viewpoint images.

<2. Embodiment of Present Disclosure>

An exemplary medical stereoscopic observation system according to an embodiment of the present disclosure will be described below.

[2.1. External Appearance of Medical Stereoscopic Observation Apparatus]

Figure 2:
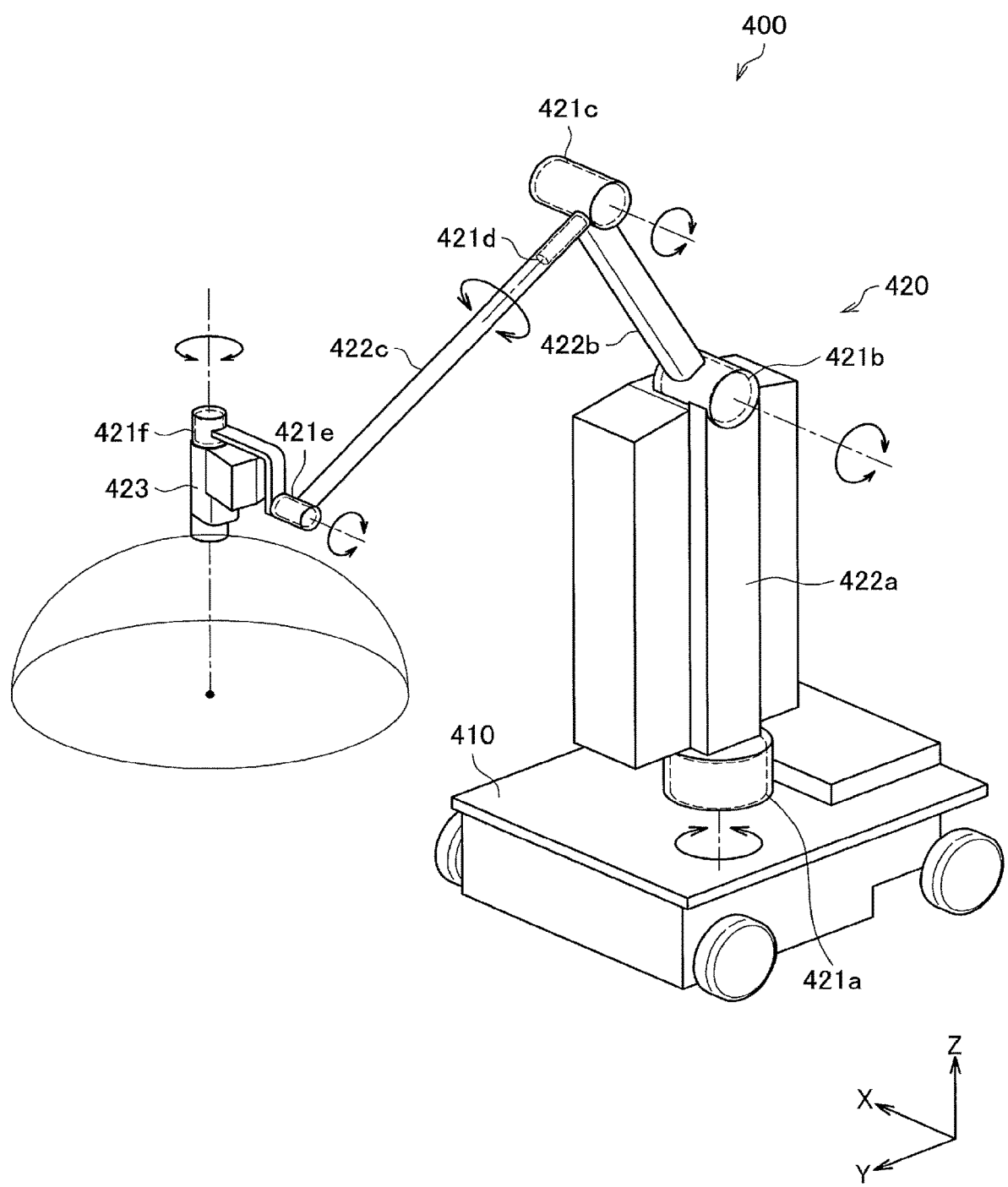
FIG. 2 is a schematic diagram illustrating an exemplary external appearance of a medical stereoscopic observation apparatus according to the same embodiment.

First, in the medical stereoscopic observation system according to an embodiment of the present disclosure, as an example of an operation video microscope apparatus (that is, a medical stereoscopic observation apparatus) that acquires image data (that is, a viewpoint image) for displaying an imaging target as a 3D image, a schematic configuration of an operation video microscope apparatus including an arm will be described with reference to FIG. 2. FIG. 2 is a schematic diagram illustrating an exemplary external appearance of the medical stereoscopic observation apparatus according to an embodiment of the present disclosure.

Referring to FIG. 2, the operation video microscope apparatus 400 that is an example of the medical stereoscopic observation apparatus according to the present embodiment includes a base unit 410 and an arm unit 420. The base unit 410 serves as the base of the operation video microscope apparatus 400, and the arm unit 420 extends from the base unit 410. Although not illustrated in FIG. 2, a control unit that controls the operation video microscope apparatus 400 in an integrated manner may be installed in the base unit 410, and driving of the arm unit 420 may be controlled by the control unit. For example, the control unit is configured with various kinds of signal processing circuits such as a central processing unit (CPU) or a digital signal processor (DSP).

The arm unit 420 includes a plurality of joint units 421*a* to 421*f*, a plurality of links 422*a* to 422*c* that are connected with one another by the joint units 421*a* to 421*f*, and an imaging unit 423 installed at the front edge of the arm unit 420.

The links 422*a* to 422*c* are rod-like members, one end of the link 422*a* is connected with the base unit 410 through the joint unit 421*a*, the other end of the link 422*a* is connected with one end of the link 422*b* through the joint unit 421*b*, and the other end of the link 422*b* is connected with one end of the link 422*c* through the joint units 421*c* and 421*d*. Further, the imaging unit 423 is connected to the front edge of the arm unit 420, that is, the other end of the link 422*c* through the joint units 421*e* and 421*f*. As described above, the arm shape extending from the base unit 410 is configured such that the base unit 410 serves as a support point, and the ends of the plurality of links 422*a* to 422*c* are connected with one another through the joint units 421*a* to 421*f*.

The imaging unit 423 is a unit that acquires an image of an imaging target, and may be configured with, for example, a camera that images, for example, a moving image or a still image. The position and posture of the imaging unit 423 are controlled by controlling driving of the arm unit 420. In the present embodiment, the imaging unit 423 images, for example, some regions of the body of a patient serving as the medical procedure part. As described above, in the operation video microscope apparatus 400 according to the present embodiment, the imaging unit 423 is configured to be able to acquire an image from a plurality of different viewpoints (that is, image data for displaying an imaging target as a 3D image), for example, such as a stereo camera.

Here, description of the operation video microscope apparatus 400 will continue with coordinate axes defined as illustrated in FIG. 2. Further, a vertical direction, a longitudinal direction, and a horizontal direction are defined according to the coordinate axes. In other words, a vertical direction with respect to the base unit 410 installed on the floor is defined as a z axis direction and a vertical direction. Further, a direction along which the arm unit 420 extends from the base unit 410 as a direction orthogonal to the z axial (that is, a direction in which the imaging unit 423 is positioned with respect to the base unit 410) is defined as a y axis direction and a longitudinal direction. Furthermore, a direction that is orthogonal to the y axis and the z axis is an x axis direction and a horizontal direction.

The joint units 421*a* to 421*f* connect the links 422*a* to 422*c* to be rotatable. Each of the joint units 421*a* to 421*f* includes a rotation mechanism that includes an actuator and is rotationally driven on a certain rotary axis according to driving of the actuator. By controlling rotary driving in each of the joint units 421*a* to 421*f*, for example, it is possible to control driving of the arm unit 420 to extend or shorten (fold) the arm unit 420. Further, as described above, since the joint units 421*a* to 421*f* according to the present embodiment include the rotation mechanism, in the following description, driving control of the joint units 421*a* to 421*f* specifically means controlling a rotational angle and/or generated torque (torque generated by the joint units 421*a* to 421*f*) of the joint units 421*a* to 421*f*.

In the example shown in FIG. 2, the operation video microscope apparatus 400 includes the 6 joint units 421*a* to 421*f*, and implements 6 degrees of freedom with regard to driving of the arm unit 420. Specifically, as illustrated in FIG. 2, the joint units 421*a*, 421*d*, and 421*f* are installed such that the long axis directions of the links 422*a* to 422*c* connected thereto and the imaging direction of the imaging unit 423 connected thereto are set as the rotary axis direction, and the joint units 421*b*, 421*c*, and 421*e* are installed such that an x axis direction serving as a direction in which connection angles of the links 422*a* to 422*c* and the imaging unit 423 connected thereto are changed within a y-z plane (a plane specified by the y axis and the z axis) is set as the rotary axis direction. As described above, in the present embodiment, the joint units 421*a*, 421*d*, and 421*f* have a function of performing yawing, and the joint units 421*b*, 421*c*, and 421*e* have a function of performing pitching.

As the above-described configuration of the arm unit 420 is provided, the operation video microscope apparatus 400 can implement the 6 degrees of freedom on driving of the arm unit 420, and thus can freely move the imaging unit 423 within a movable range of the arm unit 420. FIG. 2 illustrates a hemisphere as an exemplary movable range of the imaging unit 423. When the central point of the hemisphere is the imaging center of the medical procedure part imaged by the imaging unit 423, the medical procedure part can be imaged at various angles by moving the imaging unit 423 on the spherical surface of the hemisphere in a state in which the imaging center of the imaging unit 423 is fixed to the central point of the hemisphere.

The viewpoint images imaged from a plurality of viewpoints by the imaging unit 423 are transmitted to an image processing apparatus (not illustrated) as a video signal. Further, as described above, the image processing apparatus may be installed in the operation video microscope apparatus 400 or may be attached to the operation video microscope apparatus 400 as an external apparatus.

As a specific example, the image processing apparatus may be installed in the operation video microscope apparatus 400 such that the image processing apparatus is installed in the base unit 410 of the operation video microscope apparatus 400. In this case, the viewpoint images imaged by the imaging unit 423 are transmitted to the image processing apparatus installed in the base unit 410 via a cable installed in the arm unit 420 along the arm unit 420. Then, the image processing apparatus performs various kinds of image processing on the transmitted viewpoint images so that the left eye image and the right eye image are displayed on the display device.

[2.2. Functional Configuration of Image Processing Apparatus]

Next, an exemplary functional configuration of the image processing apparatus that performs various kinds of image processing on the viewpoint images imaged from a plurality of viewpoints by the imaging unit and outputs the left eye image and the right eye image in the medical stereoscopic observation system according to the present embodiment will be described.

Figure 3:
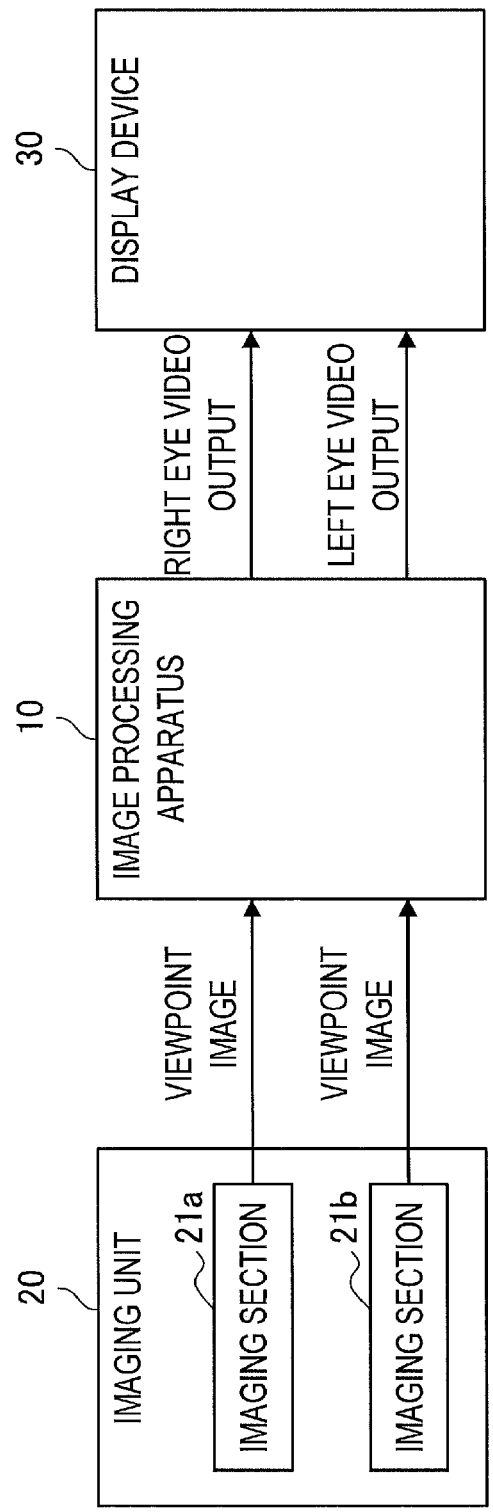
FIG. 3 is a block diagram illustrating an exemplary schematic functional configuration of a medical stereoscopic observation system according to the same embodiment.

For example, FIG. 3 is a block diagram illustrating an exemplary schematic functional configuration of the medical stereoscopic observation system according to the present embodiment, and illustrates an exemplary functional configuration focusing on an operation in which the image processing apparatus acquires the viewpoint images, and outputs the left eye image and the right eye image. In other words, the present description will proceed focusing on an imaging unit 20 that images an imaging target from a plurality of viewpoints and acquires viewpoint images, an image processing apparatus 10 that performs image processing on the imaged viewpoint images, and a display device 30 that displays an image obtained by performing image processing.

As illustrated in FIG. 3, the imaging unit 20 includes a plurality of imaging sections 21*a* and 21*b* capable of capturing a moving image. Each of the imaging sections 21*a* and 21*b* sequentially images an imaging target from a different viewpoint in units of certain frames, includes the viewpoint image imaged in units of frames in a video signal transmission frame for transmitting the viewpoint image, and outputs the resulting video signal transmission frame to the image processing apparatus 10 positioned at a subsequent stage. In the following description, when the imaging sections 21*a* and 21*b* are not particularly distinguished from each other, they are also referred to simply as an "imaging section 21." The viewpoint image that is included in the video signal transmission frame and then output to the image processing apparatus 10 corresponds to an example of "input image data."

The image processing apparatus 10 acquires the video signal transmission frame from each of the imaging sections 21*a* and 21*b*, and performs various kinds of image processing on the viewpoint images stored in each of the video signal transmission frames. Then, the image processing apparatus 10 outputs the viewpoint images obtained by performing the image processing to the display device 30 as the left eye image and the right eye image.

Figure 4:
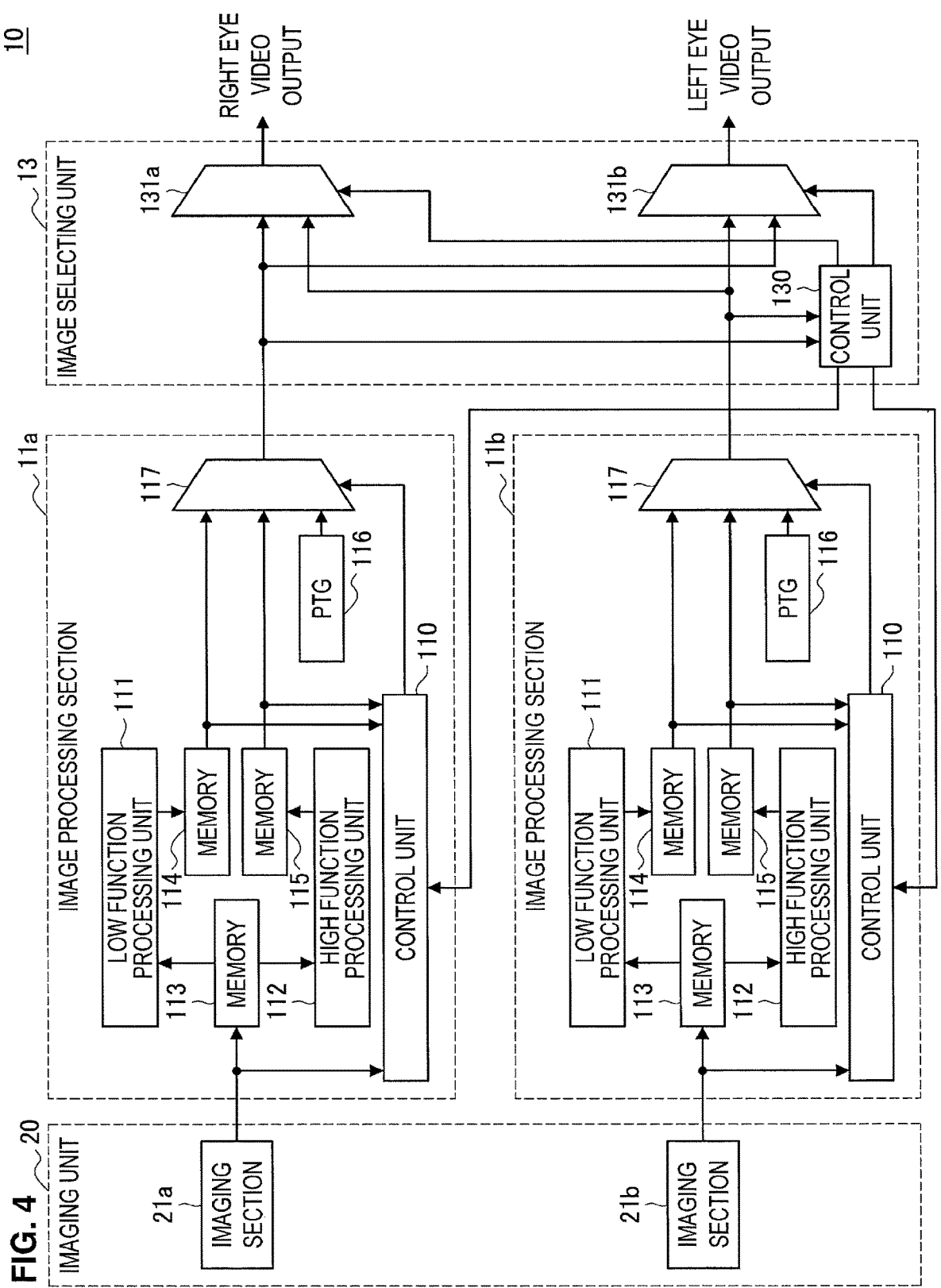
FIG. 4 is a block diagram illustrating an exemplary functional configuration of an image processing apparatus in a medical stereoscopic observation system according to the same embodiment.

Here, a functional configuration of the image processing apparatus 10 will be described in further detail with reference to FIG. 4. FIG. 4 is a block diagram illustrating an exemplary functional configuration of the image processing apparatus 10 in the medical stereoscopic observation system according to the present embodiment.

As illustrated in FIG. 4, the image processing apparatus 10 includes image processing sections 11*a* and 11*b* and an image selecting unit 13.

In the image processing apparatus 10 according to the present embodiment, the imaging section 21*a* includes the viewpoint images imaged in units of frames in the video signal transmission frame, and outputs the resulting video signal transmission frame to the image processing section 11*a* as described above. The image processing section 11*a* is a component that acquires the video signal transmission frame from the imaging section 21*a* and performs image processing on the viewpoint image stored in the video signal transmission frame.

Similarly, the imaging section 21*b* includes the viewpoint images imaged in units of frames in the video signal transmission frame, and outputs the resulting video signal transmission frame to the image processing section 11*b*. The image processing section 11*b* is a component that acquires the video signal transmission frame from the imaging section 21*b* and performs image processing on the viewpoint image stored in the video signal transmission frame.

At this time, in the image processing apparatus 10 according to the present embodiment, each of the imaging sections 21*a* and 21*b* stores a control signal (hereinafter, also referred to as a "status signal") indicating an update status of the viewpoint image in a certain region of the video signal transmission frame for transmitting the viewpoint image imaged in units of frames.

For example, FIG. 5 is a diagram illustrating an exemplary schematic data structure of the video signal transmission frame in the image processing apparatus 10 according to the present embodiment. As illustrated in FIG. 5, the video signal transmission frame includes a status signal storage field for storing the status signal. In the medical stereoscopic observation system according to the present embodiment, the status signal indicating the update status of the viewpoint image and the status signal indicating process content of image processing performed on the viewpoint image are stored in the video signal transmission frame.

As the status signal indicating the update status of the viewpoint image, for example, a signal in which information is updated for each frame such as a counter signal in which a count is increased by the update of the viewpoint image may be used. Since the status signal indicating the update status of the viewpoint image is stored in the video signal transmission frame as described above, the configurations of the subsequent stage of acquiring the video signal transmission frame can check whether or not the viewpoint image has been properly updated with reference to the status signal included in the video signal transmission frame.

The details of the status signal indicating process content of image processing performed on the viewpoint image will be separately described later.

Next, the details of the image processing sections 11*a* and 11*b* will be described. The image processing sections 11*a* and 11*b* have the same configuration. Thus, a functional configuration of the image processing section 11*a* will be described in detail, but a detailed description of the image processing section 11*b* is omitted. Hereinafter, when the image processing sections 11*a* and 11*b* are not particularly distinguished from each other, they are also referred to simply as an "image processing section 11." Further, one of the image processing sections 11*a* and 11*b* corresponds to an example of a "first image processing section," and the other corresponds to an example of a "second image processing section."

The image processing section 11*a* includes a low function processing unit 111, a high function processing unit 112, memories 113, 114, and 115, a pattern image generating unit (PTG) 116, and a selecting circuit 117.

The memory 113 is a holding unit (buffer) that temporarily holds the video signal transmission frame which is sequentially output from the imaging section 21*a* in units of frames. The video signal transmission frame output from the imaging section 21*a* is held in the memory 113. The video signal transmission frame held in the memory 113 is read from the low function processing unit 111 and the high function processing unit 112 which will be described later.

Each of the low function processing unit 111 and the high function processing unit 112 is a component for sequentially reading the video signal transmission frame held in the memory 113 and performing certain image processing on the viewpoint image stored in the video signal transmission frame. The low function processing unit 111 and the high function processing unit 112 are configured to perform different image processing on the viewpoint image in the video signal transmission frame read from the memory 113.

For example, the high function processing unit 112 may perform image analysis on the viewpoint image, extract a target (for example, a specific part, a lesion part, or the like) satisfying a specific condition from the viewpoint image, and perform, for example, a so-called emphasis process of coloring the extracted target. As another example, the high function processing unit 112 causes an image imaged by another imaging device such as a computed tomography (CT) or magnetic resonance imaging (MRI) device to be superimposed (fused) on the acquired viewpoint image. As another example, the high function processing unit 112 may extract a component of special light (a component having a wavelength having a certain band) from a viewpoint image imaged using special light as in fluorescent photography and form an image. The above-described image processing is merely an example, and does not limit content of image processing performed on the viewpoint image by the high function processing unit 112.

On the other hand, the low function processing unit 111 is configured to perform more simplified image processing than the high function processing unit 112 on the viewpoint image read from the memory 113. As a specific example, the low function processing unit 111 may be configured to perform minimal image processing so that the read viewpoint image is displayed on the display device 30 as an electronic image.

As described above, the image processing section 11*a* includes a plurality of image processing units (that is, the low function processing unit 111 and the high function processing unit 112) that perform different image processing on the viewpoint image acquired by the imaging section 21*a*. In the present description, the example in which the low function processing unit 111 and the high function processing unit 112 are installed as a plurality of image processing units included in the image processing section 11*a* has been described, but a plurality of image processing units are not limited to necessarily have the same configuration. In other words, content of image processing performed on the viewpoint image by the image processing units is not particularly limited as long as the image processing units are configured to perform different image processing on the acquired viewpoint image.

As described above, the high function processing unit 112 performs certain image processing the viewpoint image stored in the video signal transmission frame read from the memory 113. Then, the high function processing unit 112 stores the viewpoint image that has undergone the image processing in the video signal transmission frame, and stores the status signal indicating process content of image processing performed on the viewpoint image in the status signal storage field of the video signal transmission frame as illustrated in FIG. 5. The high function processing unit 112 holds the video signal transmission frame updated as described above in the memory 115. The memory 115 is a holding unit (buffer) that holds the video signal transmission frame storing the image-processed viewpoint image output from the high function processing unit 112.

Similarly, the low function processing unit 111 performs certain image processing on the viewpoint image stored in the video signal transmission frame read from the memory 113. Then, the low function processing unit 111 stores the image-processed viewpoint image in the video signal transmission frame, and stores the status signal indicating process content of image processing performed on the viewpoint image in the status signal storage field of the video signal transmission frame. The low function processing unit 111 holds the video signal transmission frame updated as described above in the memory 114. The memory 114 is a holding unit (buffer) that holds the video signal transmission frame storing the image-processed viewpoint image output from the low function processing unit 111.

The PTG 116 is a component that generates a pattern generation image. The pattern generation image is an image output instead of the viewpoint image when an abnormality occurs, for example, the viewpoint image is not updated, and thus it is difficult to output the viewpoint image. The PTG 116 outputs the generated pattern image to the selecting circuit 117.

The selecting circuit 117 is a configuration that switches the signal (for example, the video signal transmission frame) output from the image processing section 11a. The selecting circuit 117 outputs any one of the video signal transmission frame held in the memory 114, the video signal transmission frame held in the memory 115, and the pattern generation image output from the PTG 116 to the image selecting unit 13 positioned at the stage subsequent to the image processing section 11a based on control from a control unit 110.

The control unit 110 monitors an input of the video signal transmission frame to the memory 113 from the imaging section 21a and an output of the video signal transmission frame from the memories 114 and 115, and controls switching of an output by the selecting circuit 117 according to a monitoring result. Further, the control unit 110 may control switching of an output by the selecting circuit 117 based on feedback from a control unit 130 of the image selecting unit 13 which will be described later. The details of the control of the control unit 110 related to the switching of the output by the selecting circuit 117 will be separately described later.

Next, a configuration of the image selecting unit 13 will be described. The image selecting unit 13 includes selecting circuits 131a and 131b and the control unit 130.

The selecting circuit 131a video-outputs one of the signal (for example, the video signal transmission frame) output from the image processing section 11a and the signal output from the image processing section 11b as the right eye image based on control from the control unit 130. Similarly, the selecting circuit 131b video-outputs one of the signal (for example, the video signal transmission frame) output from the image processing section 11a and the signal output from the image processing section 11b as the left eye image based on control from the control unit 130.

The control unit 130 monitors the signals output from the image processing sections 11a and 11b, and recognizes the statuses of the image processing sections 11a and 11b according to the monitoring result. Specifically, the control unit 130 recognizes the update statuses of the viewpoint images output from the image processing sections 11a and 11b and processing content of the image processing performed on the viewpoint images based on the status signals stored in the video signal transmission frames output from the image processing sections 11a and 11b.

Then, the control unit 130 controls switching of the outputs by the selecting circuits 131a and 131b according to the recognized statuses of the image processing sections 11a and 11b. Further, based on the monitoring result of the signal from one image processing section 11 of the image processing sections 11a and 11b, the control unit 130 controls an operation of the other image processing section 11 by feeding information back to the other image processing section 11 according to the status of one image processing section 11. Thus, the other image processing section 11 recognizes the status of one image processing section 11 based on the information fed back from the control unit 130 and can switch an output according to the recognized status.

A system configuration of the medical stereoscopic observation system and a configuration of the image processing apparatus 10 are not particularly limited as long as it is possible to implement the above-described functions of the image processing apparatus 10. As a specific example, the imaging unit 20 and the image processing apparatus 10 may be integrally configured as the operation video microscope apparatus 400 described above with reference to FIG. 2. Another example, the image processing apparatus 10 may be installed in the display device 30. The image processing sections 11a and 11b of the image processing apparatus 10 and the image selecting unit 13 may be installed in different apparatuses.

The exemplary functional configuration of the image processing apparatus that performs various kinds of image processing on the viewpoint images imaged by the imaging unit and outputs the left eye image and the right eye image in the medical stereoscopic observation system according to the present embodiment has been described so far with reference to FIGS. 2 to 5.

[2.3. Details of Switching Control]

Next, the details of the output switching control performed by the image processing apparatus 10 according to the present embodiment will be described, focusing particularly on control by the control unit 110 of each of the image processing sections 11a and 11b illustrated in FIG. 3 and control by the control unit 130 of the image selecting unit 13.

<<2.3.1. Switching Control in Image Selecting Unit>>

First, the details of the switching control performed by the control unit 130 of the image selecting unit 13 will be described with reference to FIG. 6. FIG. 6 illustrates an example of a control table d10 used when the control unit 130 of the image selecting unit 13 controls switching of the outputs by the selecting circuits 131a and 131b and feedback of information to the image processing sections 11a and 11b.

As illustrated in FIG. 6, the control table d10 includes an item number d11 identifying various kinds of control, input information d12, control feedback d13, output control d14, and a default setting d15.

The input information d12 includes a left input d121 and a right input d122. The left input d121 indicates a type of a signal output from the image processing section 11b. The right input d122 indicates a type of a signal output from the image processing section 11a. As illustrated in FIG. 6, at least one of "high function processing image," "low function processing image," and "pattern generation image" can be set to the left input d121 and the right input d122 as a type of signal.

Among the types of the signal that can be set to the left input d121 and the right input d122, "high function processing image" indicates that the viewpoint image that has undergone the image processing performed by the high function processing unit 112 of the image processing section 11 is input as an input signal from the image processing section 11. Similarly, "low function processing image" indicates that the viewpoint image that has undergone the image processing performed by the low function processing unit 111 of the image processing section 11 is input as the input signal from the image processing section 11. Further, the "pattern generation image" indicates that the pattern generation image generated by the PTG 116 of the image processing section 11 is input as the input signal from the image processing section 11.

The control unit 130 preferably recognizes the type of the signal output from the image processing section 11 based on the status signal indicating the processing content stored in the video signal transmission frame acquired from each image processing section 11.

The control feedback d13 indicates content of feedback control which the control unit 130 performs on the image processing sections 11a and 11b according to the input information d12. As illustrated in FIG. 6, one of "autonomous selection" and "low function process selection" can be fed back to the image processing sections 11a and 11b.

In the feedback control on the image processing sections 11a and 11b, the "autonomous selection" indicates that the control unit 130 controls the operations of the image processing sections 11a and 11b so that each of the image processing sections 11a and 11b selects a type of signal to be output according to its status. The "low function process selection" indicates that the control unit 130 controls the operations of the image processing sections 11a and 11b so that each of the image processing sections 11a and 11b outputs the viewpoint image obtained by performing the image processing through the low function processing unit 111.

The output control d14 includes a left output d141 and a right output d142. The left output d141 indicates content of control on the selecting circuit 131b that outputs the left eye image by the control unit 130. Similarly, the right output d142 indicates content of control on the selecting circuit 131a that outputs the right eye image by the control unit 130. As illustrated in FIG. 6, an instruction of one of "own system selection" and "other system selection" is given to the selecting circuits 131a and 131b.

Of the instructions given to the selecting circuits 131a and 131b, the "own system selection" indicates that the control unit 130 instructs each of the selecting circuits 131a and 131b to select and output an input of its own system. The input of its own system indicates an input from the image processing section 11 that is previously associated with the selecting circuits 131a and 131b. Specifically, when "own system selection" is instructed, the selecting circuit 131a outputs an input from the image processing section 11a of the image processing sections 11a and 11b as the right eye image. Similarly, when "own system selection" is instructed, the selecting circuit 131b outputs an input from the image processing section 11b of the image processing sections 11a and 11b as the left eye image.

Further, the "other system selection" indicates that the control unit 130 instructs each of the selecting circuits 131a and 131b to select and output an input of another system. The input of another system indicates an input from another image processing section 11 different from the image processing section 11 associated as its own system. In other words, when "other system selection" is instructed, the selecting circuit 131a outputs an input from the image processing section 11b of the image processing sections 11a and 11b as the right eye image. Similarly, when "other system selection" is instructed, the selecting circuit 131b outputs an input from the image processing section 11a of the image processing sections 11a and 11b as the left eye image.

The default setting d15 indicates control set as a default among various kinds of control identified by the item number d11. For example, in the example illustrated in FIG. 6, control indicated by "No. 1" in the item number d11 is set as a default. The control indicated by the default setting d15 is applied as, for example, an initial setting when the image processing apparatus 10 is activated.

<<2.3.2. Switching Control in Image Processing Section>>

Next, the details of the switching control by the control unit 110 of each of the image processing sections 11a and 11b will be described with reference to FIG. 7. FIG. 7 illustrates an example of a control table d20 used when the control unit 110 of each of the image processing sections 11a and 11b controls switching of the output by the selecting circuit 117.

As illustrated in FIG. 7, the control table d20 includes an item number d21 identifying various kinds of control, an update status d22, a feedback input d23, output selection d24, and a default setting d25.

The update status d22 includes an input update status d221, a low function process output update status d222, and a high function process output update status d223. The input update status d221 indicates an update status of a viewpoint image input from the corresponding imaging section 21 to the image processing section 11. In other words, at least one of "updated" and "not updated" can be set to the input update status d221 as the update status of the input viewpoint image.

The low function process output update status d222 indicates the update status of the viewpoint image obtained by performing image processing through the low function processing unit 111. Similarly, the high function process output update status d223 indicates the update status of the viewpoint image obtained by performing image processing through the high function processing unit 112. At least one of "OK," "NG" and "Don't care" can be set to the low function process output update status d222 and the high function process output update status d223 as the update status of the viewpoint image obtained by performing image processing through each image processing unit.

Among the update statuses of the viewpoint images obtained by performing image processing through the image processing units, "OK" indicates that the image-processed viewpoint image has been properly updated. "NG" indicates that a certain abnormality has occurred in the process of image processing on the viewpoint image, and the viewpoint image has not been properly updated. "Don't care" indicates that it is not a determination target.

The feedback input d23 indicates content of feedback control from the control unit 130 of the image selecting unit 13. As described above, at least one of "autonomous selection" and "low function process selection" can be fed back from the control unit 130 to each of the image processing sections 11. "Don't care" indicates that it is not a determination target.

The output selection d24 indicates content of control on the selecting circuit 117 by the control unit 110. As illustrated in FIG. 7, an instruction of at least one of "high function processing image selection," "low function processing image selection," and "pattern generation image selection" is given to the selecting circuit 117.

Among the instructions given to the selecting circuit 117, "high function processing image selection" indicates that the control unit 110 instructs the selecting circuit 117 to output the video signal transmission frame (that is, the video signal transmission frame held in the memory 115) output from the high function processing unit 112. Similarly, "low function processing image selection" indicates that the control unit 110 instructs the selecting circuit 117 to output the video signal transmission frame (that is, the video signal transmission frame held in the memory 114) output from the low function processing unit 111. Further, "pattern generation image selection" indicates that the control unit 110 instructs the selecting circuit 117 to output the pattern generation image generated by the PTG 116.

The default setting d25 indicates control set as a default among various kinds of control identified by the item number d21. For example, in the example illustrated in FIG. 7, control indicated by "No. 2" in the item number d21 is set as a default. The control indicated by the default setting d25 is applied as, for example, an initial setting when the image processing apparatus 10 is activated.

<<2.3.3. First Specific Example of Switching Control>>

Next, detailed content of the output switching control performed by the image processing apparatus 10 according to the present embodiment will be described using specific examples.

First, as a first specific example, an example of an operation of the image processing apparatus 10 when it has become difficult for the high function processing unit 112 of the image processing section 11a to perform an operation with the increase of ambient temperature will be described. At this time, it is assumed that the viewpoint image input from the imaging section 21a has been properly updated, and the low function processing unit 111 of the image processing section 11a is in a normally operable state. Further, "autonomous selection" is assumed to be fed back from the control unit 130 of the image selecting unit 13 to the control unit 110 of the image processing section 11a.

In this case, first, the control unit 110 of the image processing section 11a detects that the output from the high function processing unit 112 has not been updated (that is, a certain abnormality has occurred in the high function processing unit 112) based on a monitoring result of the output of the video signal transmission frame from the memory 115.

Upon receiving the monitoring result, the control unit 110 of the image processing section 11a sets the high function process output update status d223 to "NG." At this time, an instruction to output the video signal transmission frame output from the low function processing unit 111 is given to the selecting circuit 117 based on control indicated by "No. 4" in the item number d21 in the control table d20 illustrated in FIG. 7.

Upon receiving this instruction, the selecting circuit 117 outputs the video signal transmission frame that is output from the low function processing unit 111 and held in the memory 114 to the image selecting unit 13 at the subsequent stage. At this time, the status signal indicating that the image processing has been performed by the low function processing unit 111 is set to the video signal transmission frame output from the selecting circuit 117.

Then, the control unit 130 of the image selecting unit 13 recognizes that the output from the image processing section 11a has been switched to the video signal transmission frame output from the low function processing unit 111 based on the monitoring result of the status signal in the video signal transmission frame output from the image processing section 11a. In other words, at this point in time, the state in which the video signal transmission frame from the low function processing unit 111 is output from the image processing section 11a, and the video signal transmission frame from the high function processing unit 112 is output from the image processing section 11b is made. For this reason, the control unit 130 feeds "low function process selection" back to at least the image processing section 11b based on control indicated by "No. 2" in the item number d11 in the control table d10 illustrated in FIG. 6. At this time, the state in which the viewpoint image input from the imaging section 21b to the image processing section 11b has been properly updated, and thus the high function processing unit 112 and the low function processing unit 111 of the image processing section 11b are normally operable is assumed to be made.

Upon receiving "low function process selection" fed back from the control unit 130, the control unit 110 of the image processing section 11b controls the selecting circuit 117 based on control indicated by "No. 3" in the item number d21 in the control table d20 illustrated in FIG. 7. In other words, the control unit 110 of the image processing section 11b gives an instruction to output the video signal transmission frame output from the low function processing unit 111.

Upon receiving this instruction, the selecting circuit 117 outputs the video signal transmission frame that is output from the low function processing unit 111 and held in the memory 114 to the image selecting unit 13 at the subsequent stage.

Through the above control, the video signal transmission frame from the low function processing unit 111 is output from both of the image processing sections 11a and 11b.

At this time, the control unit 130 controls the selecting circuits 131a and 131b based on control indicated by "No. 5" in the item number d11 in the control table d10 illustrated in FIG. 6. In other words, since "own system selection" is set to both of the left output d141 and the right output d142, the selecting circuits 131a and 131b select and output the input of their own system.

More specifically, in this case, the selecting circuit 131a outputs the video signal transmission frame which has been acquired as the input from the image processing section 11a and output from the low function processing unit 111 of the image processing section 11a as the right eye image. Similarly, the selecting circuit 131b outputs the video signal transmission frame that has been acquired as the input from the image processing section 11b and output from the low function processing unit 111 of the image processing section 11b as the left eye image.

Through the above configuration, when the high function processing unit 112 in one of the image processing sections 11a and 11b is switched to the low function processing unit 111, the image processing apparatus 10 performs control such that the high function processing unit 112 in the other is switched to the low function processing unit 111. In other words, according to the image processing apparatus 10 of the present embodiment, even when an abnormality occurs in one of the image processing sections 11, control is performed such that the left eye image matches the right eye image, and thus the user can observe the 3D image.

<<2.3.4. Second Specific Example of Switching Control>>

Next, as a second specific example, an example of an operation of the image processing apparatus 10 when an abnormality occurs in the imaging section 21b of the imaging section 21a and the imaging section 21b, and the update of the viewpoint image to be input to the image processing section 11b is suspended will be described. At this time, the low function processing unit 111 and the high function processing unit 112 of the image processing section 11b are assumed to be in a normally operable state. Further, "autonomous selection" is assumed to be fed back from the control unit 130 of the image selecting unit 13 to the control unit 110 of the image processing section 11b.

In this case, first, the control unit 110 of the image processing section 11b detects that the input from the imaging section 21b has not been updated (that is, a certain abnormality has occurred in the imaging section 21b) based on a monitoring result of the input of the video signal transmission frame to the memory 113.

Upon receiving the monitoring result, the control unit 110 of the image processing section 11b set the input update status d221 to "not updated." At this time, an instruction to output the pattern generation image generated by the PTG 116 is given to the selecting circuit 117 based on control indicated by "No. 1" in the item number d21 in the control table d20 illustrated in FIG. 7.

Upon receiving this instruction, the selecting circuit 117 of the image processing section 11b outputs the pattern generation image output from the PTG 116 to the image selecting unit 13 at the subsequent stage.

Then, the control unit 130 of the image selecting unit 13 recognizes that the output from the image processing section 11b has been switched to the pattern generation image based on the monitoring result of the output from the image processing section 11b. In other words, at this point in time, the video signal transmission frame from the high function processing unit 112 is output from the image processing section 11a, and the pattern generation image is output from the image processing section 11b.

For this reason, the control unit 130 controls the selecting circuits 131a and 131b based on control indicated by "No. 7" in the item number d11 in the control table d10 illustrated in FIG. 6. In other words, since "other system selection" is set to the left output d141, the selecting circuit 131b selects and outputs the input of another system (that is, the input from the image processing section 11a). Further, since "own system selection" is set to the right output d142, the selecting circuit 131a selects and outputs the input of its own system (that is, the input from the image processing section 11a).

Through the above configuration, when one of the image processing sections 11a and 11b enters the state in which it is difficult to output the image imaged by the imaging section 21, the image processing apparatus 10 performs control such that the output from the other is output as the right eye image and the left eye image. Through this control, although it is difficult to observe the 3D image, the user can observe a 2D image of the affected area serving as the imaging target.

The above description has been made in connection with the example in which an abnormality occurs in the imaging section 21, but the same applies when an abnormality occurs in both of the high function processing unit 112 and the low function processing unit 111 in one of the image processing sections 11a and 11b.

[2.4. Process]

Figure 8:
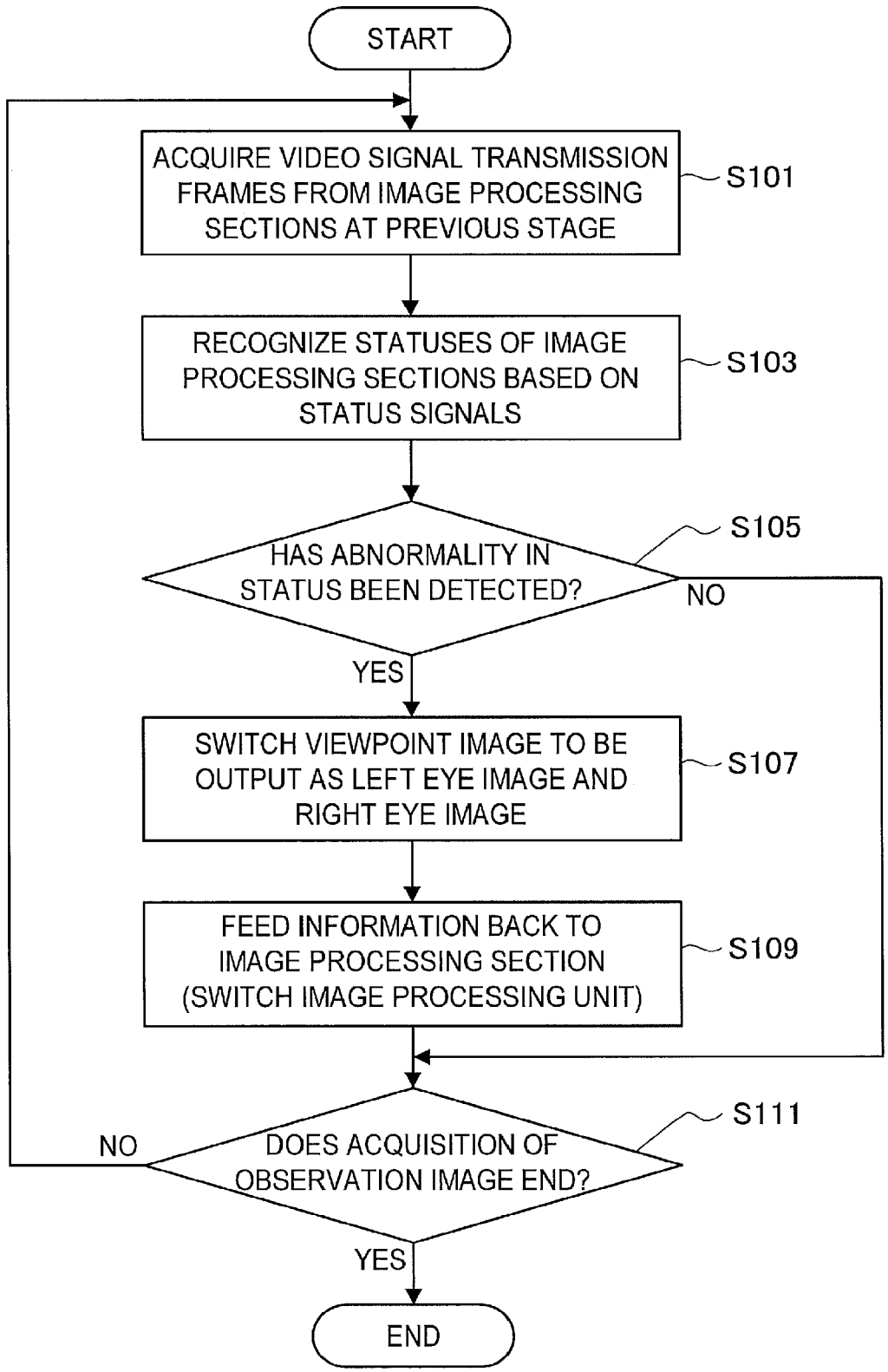
FIG. 8 is a flowchart illustrating an exemplary flow of a series of operations related to output switching control performed by an image processing apparatus according to the same embodiment.

Next, an example of a series of operations related to the output switching control performed by the image processing apparatus 10 according to the present embodiment will be described, focusing particularly on the operation of the image selecting unit 13 of the image processing apparatus 10. For example, FIG. 8 is a flowchart illustrating an example of a series of operations related to the output switching control performed by the image processing apparatus 10 according to the present embodiment.

(Step S101)

The viewpoint images imaged by the imaging sections 21 of the imaging unit 20 undergo image processing performed by the image processing sections 11 of the image processing apparatus 10, are included in the video signal transmission frame, and are output to the image selecting unit 13 of the image processing apparatus 10. At this time, the status signal according to a processing status of each component is stored in the video signal transmission frame to be output to the image selecting unit 13 through the imaging section 21 and the image processing section 11.

(Step S103)

The control unit 130 of the image selecting unit 13 monitors the signals output from the image processing sections 11, and recognizes the statuses of the image processing sections 11 according to the monitoring result. Specifically, the control unit 130 recognizes the update statuses of the viewpoint images output from the image processing sections 11 and processing content of image processing performed on the viewpoint images based on the status signals stored in the video signal transmission frames output from the image processing sections 11a and 11b.

(Step S107)

When an abnormality is detected in the status of at least one of the image processing sections 11 based on the status signals (YES in step S105), the control unit 130 controls the selecting circuits 131a and 131b such that the viewpoint image to be output as the left eye image and the right eye image is switched.

As a specific example, it is assumed that it has become difficult for one of the image processing sections 11 to update the viewpoint image and thus a pattern generation image is output. In this case, the control unit 130 controls the selecting circuits 131a and 131b such that the output from the other image processing section 11 is output as the left eye image and the right eye image.

(Step S109)

The control unit 130 may control the operation of the other image processing section 11 by feeding information back to the other image processing section 11 according to the status of one of the image processing sections 11.

As a specific example, it is assumed that an abnormality has occurred in the high function processing unit 112 in one of the image processing sections 11, and one image processing section 11 has transitioned to the status in which the viewpoint image having undergone the image processing performed by the low function processing unit 111 is output. In this case, the control unit 130 feeds certain information (for example, "low function process selection" indicated as the control feedback d13 in FIG. 6) back so that the other image processing section 11 outputs the viewpoint image that has undergone the image processing performed by the low function processing unit 111. Upon receiving the feedback given from the control unit 130, the other image processing section 11 controls the selecting circuit 117 such that the viewpoint image that has undergone the image processing performed by the low function processing unit 111 is output. As a result, the viewpoint images that have undergone the image processing performed by the low function processing unit 111 are output from the image processing sections 11, and the viewpoint image output as the left eye image matches the viewpoint image output as the right eye image.

It is needless to say that the control unit 130 need not necessarily perform the process of steps S107 and S109 unless an abnormality occurs in the statuses of the image processing sections 11 (No in step S105).

(Step S111)

The control unit 130 continuously performs the series of processes described above unless an instruction to end acquisition of an observation image by the medical stereoscopic observation system is given (that is, as long as the viewpoint images are acquired by the imaging unit 20) (NO in step S111). Then, when the instruction to end acquisition of an observation image by the medical stereoscopic observation system is given (YES in step S111), the control unit 130 ends the series of processes described above.

The example of the flow of the series of operations related to the output switching control performed by the image processing apparatus 10 according to the present embodiment has been described above with reference to FIG. 8, focusing particularly on the operation of the image selecting unit 13 of the image processing apparatus 10.

[2.5. Modified Examples]

Next, modified examples of the medical stereoscopic observation system according to an embodiment of the present disclosure will be described, focusing particularly on the image processing apparatus 10.

<<2.5.1. First Modified Example: Status Notification at Time of Switching Control>>

As described above, the control unit 130 of the image processing apparatus 10 according to the present embodiment monitors the signals output from the image processing sections 11a and 11b, and recognizes the statuses of the image processing sections 11a and 11b according to the monitoring result. Then, the control unit 130 controls switching of the image processing unit in the image processing sections 11 or switching of the viewpoint image output as the left eye image and the right eye image according to the recognized statuses of the image processing sections 11a and 11b. For this reason, the image processing apparatus 10 may be configured to report to the user a change in the status (that is, a change in the status of the image processing apparatus 10) when switching of the image processing unit in the image processing sections 11 or switching of the viewpoint image output as the left eye image and the right eye image is performed.

In this regard, as a first modified example, an exemplary configuration in which the image processing apparatus 10 reports information to the user according to a change in the status with the switching of the image processing unit in the image processing sections 11 or the switching of the viewpoint image output as the left eye image and the right eye image will be described.

As a specific example, the image processing apparatus 10 may report the change in the status with the switching of the image processing unit or the switching of the viewpoint image output as the left eye image and the right eye image through a reporting unit that reports information to the user.

For example, the reporting unit may be configured with a display device such as a display. In this case, the reporting unit reports report information to the user by causing the report information for reporting to the user the change in the status of the image processing apparatus 10 to be displayed on the display device as display information.

As another example, the reporting unit may be a device that reports certain information to the user through a lighting or blinking pattern such as a light emitting diode (LED). Further, the reporting unit may be a device that reports certain information to the user by outputting a certain sound (for example, a sound effect or a voice) such as a speaker or the like. As described above, the form of the reporting unit is not particularly limited as long as it is possible to report information to the user.

The operation of reporting information to the user through the reporting unit is preferably controlled by, for example, the control unit 130 of the image processing apparatus 10. In this case, for example, when control other than control set as a default among various kinds of controlled specified in the control table d10 illustrated in FIG. 6 is executed, the control unit 130 preferably causes the reporting unit to report report information according to the executed control. Of course, the main body of controlling the reporting unit is not limited to the control unit 130 as long as it is possible to report to the user the change in the status with the switching of the image processing unit in the image processing sections 11 or the switching of the viewpoint image output as the left eye image and the right eye image.

As another example, the notification of the change in the status of the image processing apparatus 10 may be given to the user by causing the report information to be displayed in the viewpoint image observed as the left eye image and the right eye image.

Figure 9:
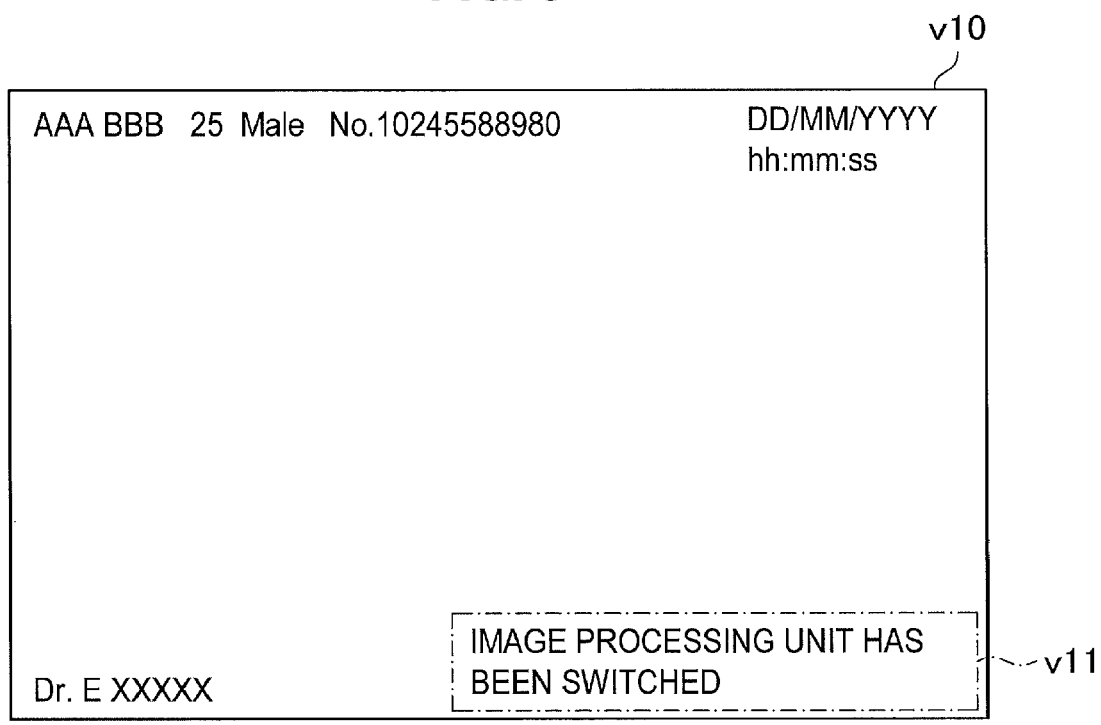
FIG. 9 is a diagram illustrating an exemplary method of reporting information indicating a status of an image processing apparatus.

For example, FIG. 9 is a diagram illustrating an exemplary notification method of information indicating the change in the status of the image processing apparatus 10, and illustrates a display example of the viewpoint image when the report information is displayed in the viewpoint image. Specifically, FIG. 9 illustrates an example of the viewpoint image observed by the user as the right eye image and the left eye image when an abnormality occurs in the high function processing unit 112 of the image processing section 11, and switching to the low function processing unit 111 is performed.

In other words, in the example illustrated in FIG. 9, report information v11 indicating that the image processing unit of the image processing section 11 has switched from the high function processing unit 112 to the low function processing unit 111 is presented in a viewpoint image v10.

The main control body is not particularly limited as long as it is possible to perform control such that the report information is presented in the viewpoint image. As a specific example, the control unit 130 of the image processing apparatus 10 may acquire the video signal transmission frames output from the image processing sections 11 and cause the report information according to the change in the status of the image processing apparatus 10 to be superimposed on the viewpoint images in the acquired video signal transmission frames.

As another example, the image processing sections 11 of the image processing apparatus 10 may cause the report information according to its own status to be superimposed on the viewpoint image serving as the processing target.

In this case, for example, the low function processing unit 111 may cause report information to be constantly superimposed on the viewpoint image output from the low function processing unit 111. Through this configuration, for example, when an abnormality occurs in the high function processing unit 112, and the viewpoint image that has undergone the image processing performed by the same low function processing unit 111 is output from the image processing section 11, the user observes the report information superimposed on the viewpoint image. For this reason, the user can recognize that the image processing unit of the image processing section 11 has switched from the high function processing unit 112 to the low function processing unit 111 based on the report information displayed on the viewpoint image.

The above-described example is merely an example, and the method and the main body of the operation related to the notification are not particularly limited as long as it is possible to report to the user the change in the status of the image processing apparatus 10.

The example of the configuration in which the image processing apparatus 10 reports information to the user according to the change in the status with the switching of the image processing unit in the image processing sections 11 or the switching of the viewpoint image output as the left eye image and the right eye image has been described above as the first modified example.

<<2.5.2. Second Modified Example: Exemplary Configuration When Image Processing is Performed in Plurality of Steps>>

Next, as a second modified example, an example of a configuration of the image processing apparatus configured to be able to switch the image processing unit in each step when the image processing on the viewpoint images acquired by the imaging unit is executed in a plurality of steps will be described. Hereinafter, the image processing apparatus according to the second modified example is also referred to as an "image processing apparatus 50" in order to distinguish it from the image processing apparatus 10 according to the above embodiment. In the present description, the image processing apparatus 50 according to the second modified example will be described focusing on a different configuration from the image processing apparatus 10 according to the above embodiment, and a detailed description of the remaining configuration is omitted.

Figure 10:
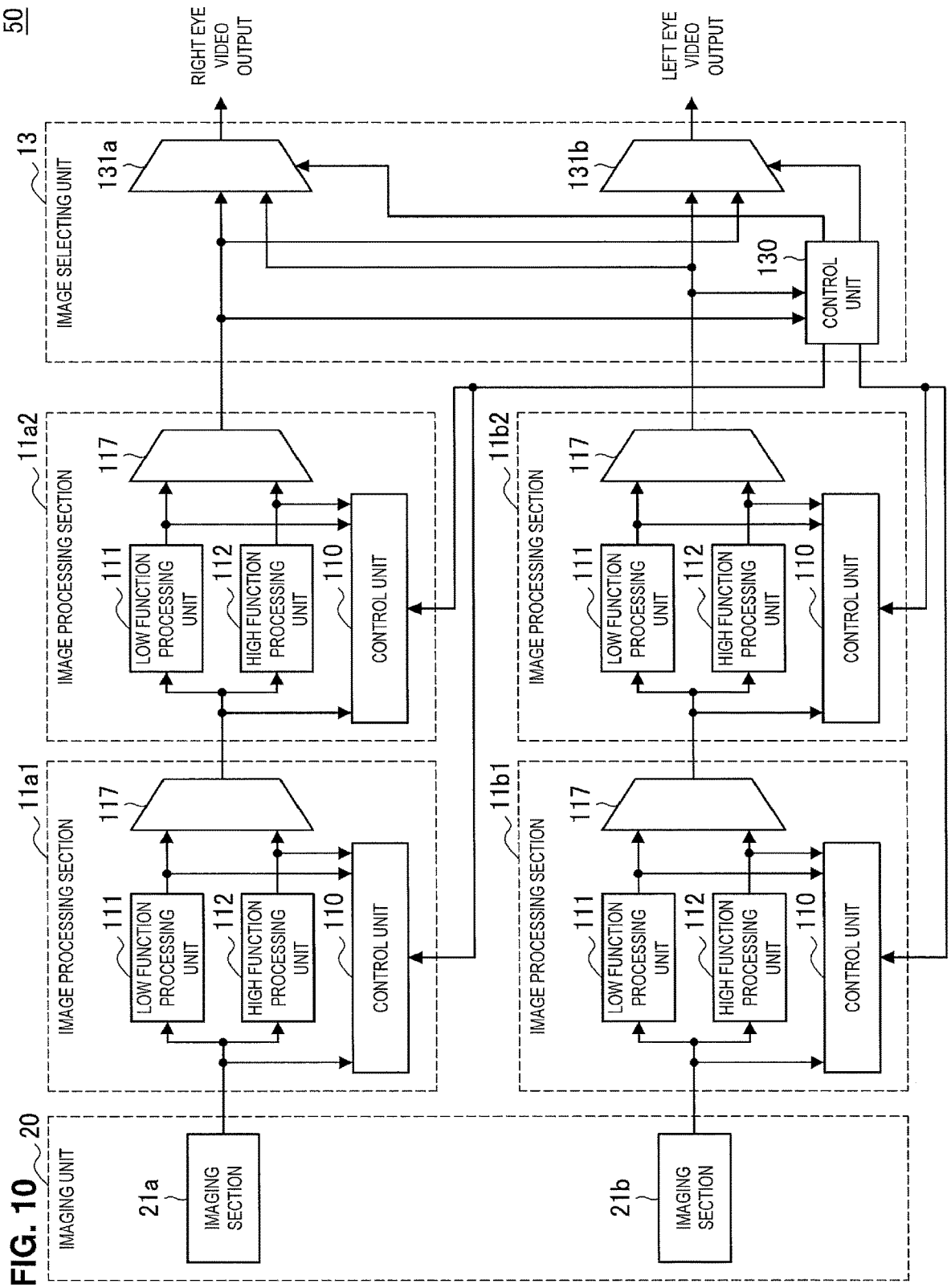
FIG. 10 is a block diagram illustrating an exemplary functional configuration of an image processing apparatus according to a second modified example.

For example, FIG. 10 is a block diagram illustrating an exemplary functional configuration of the image processing apparatus 50 according to the second modified example. In FIG. 10, each of reference numerals 11a1, 11a2, 11b1, and 11b2 corresponds to the image processing section 11 in the image processing apparatus 10 according to the above embodiment. In FIG. 10, the functional blocks of the image processing sections 11a1, 11a2, 11b1, and 11b2 are illustrated in a simplified manner by omitting illustration of some components. For this reason, hereinafter, when it is unnecessary to particularly distinguish the image processing sections 11a1, 11a2, 11b1, and 11b2 from one another, they are also referred to simply as an "image processing section 11."

In the configuration illustrated in FIG. 10, the image processing sections 11a1 and 11a2 sequentially perform image processing on the viewpoint image acquired by the imaging section 21a, and the video signal transmission frame including the image-processed viewpoint image is output to the image selecting unit 13. Similarly, the image processing sections 11b1 and 11b2 sequentially perform image processing on the viewpoint image acquired by the imaging section 21b, and the video signal transmission frame including the image-processed viewpoint image is output to the image selecting unit 13.

In other words, in the example illustrated in FIG. 10, the image processing sections 11a1 and 11b1 perform image processing of first step on the viewpoint images acquired by the imaging sections 21a and 21b, and the image processing sections 11a2 and 11b2 perform image processing of a second step on the result. Thus, in the example illustrated in FIG. 10, the image processing sections 11 are configured to cause the viewpoint images output in respective steps to match one another.

Specifically, in the image processing apparatus 50 according to the second modified example, the image processing sections 11a1 and 11b1 that perform the image processing of the first step on the viewpoint images have the same configuration (more specifically, the same image processing unit), and are configured to perform the same image processing on the viewpoint images. The image processing sections 11a2 and 11b2 that perform the image processing of the second step on the viewpoint images have the same configuration, and are configured to perform the same image processing on the viewpoint images.

Further, in the image processing apparatus 50 according to the second modified example, when an abnormality occurs in any one of the image processing sections 11, the switching of the image processing unit in the image processing section 11 is controlled in each step. As a specific example, when the image processing unit is switched in the image processing section 11a1 corresponding to the first step, the image processing apparatus 50 performs control such that the image processing unit is similarly switched in the other image processing section 11b1 corresponding to the first step. As another example, when the image processing unit is switched in the image processing section 11b2 corresponding to the second step, the image processing apparatus 50 performs control such that the image processing unit is similarly switched in the other image processing section 11a2 corresponding to second first step.

Through this control, the image processing apparatus 50 according to the second modified example can perform control such that the output viewpoint images match one another in each step of image processing performed on the viewpoint images.

In this regard, an exemplary mechanism for implementing the output switching control performed by the image processing apparatus 50 according to the second modified example will be described.

Figure 11:
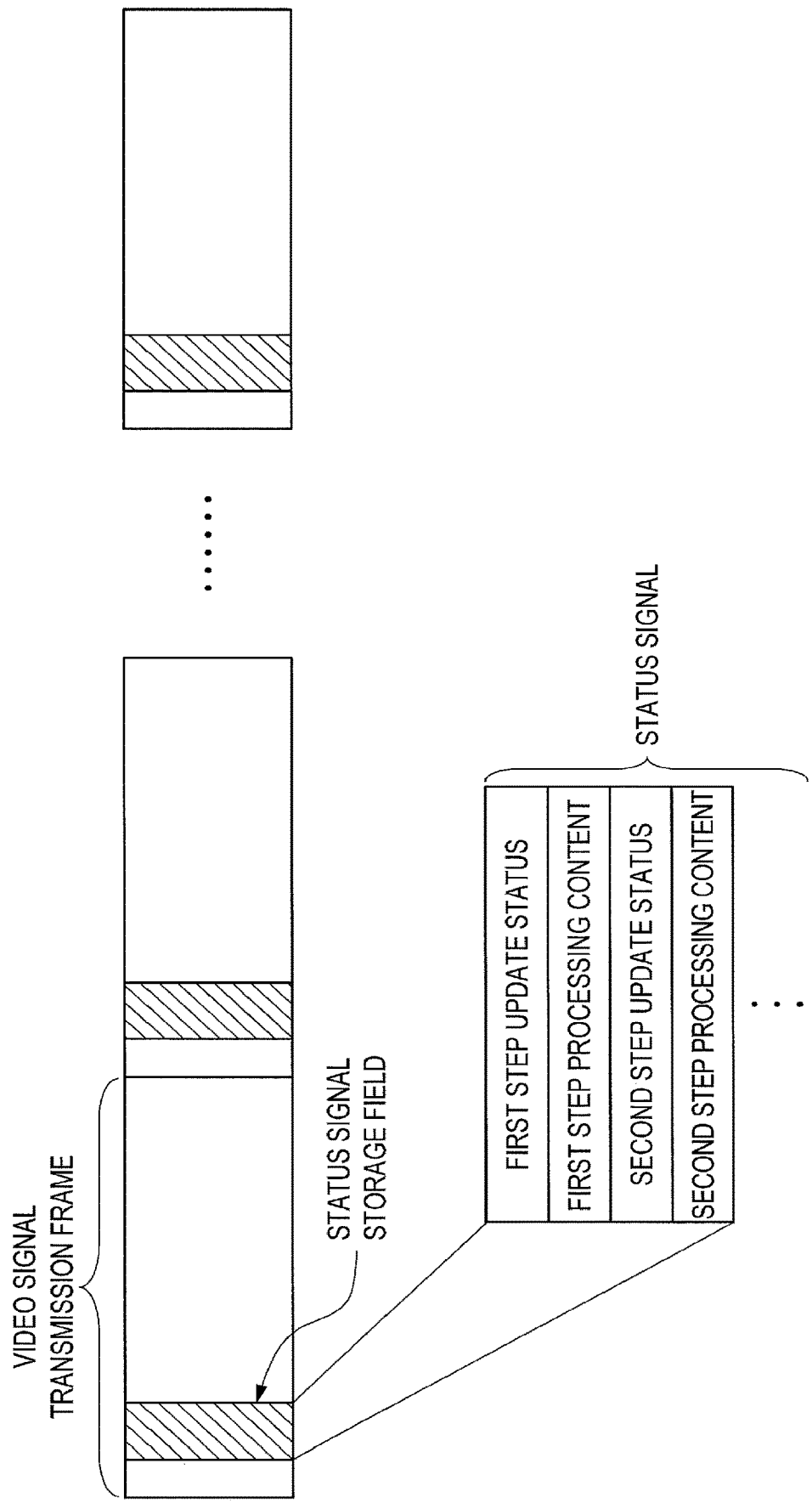
FIG. 11 is a diagram illustrating an exemplary schematic data structure of a video signal transmission frame in an image processing apparatus according to the second modified example.

First, an exemplary schematic data structure of the video signal transmission frame in the image processing apparatus 50 according to the second modified example will be described with reference to FIG. 11. FIG. 11 is a diagram illustrating an exemplary schematic data structure of the video signal transmission frame in the image processing apparatus 50 according to the second modified example.

As illustrated in FIG. 11, in the image processing apparatus 50 according to the second modified example, a status signal indicating "update status" and "processing content" is stored for each step of image processing performed on the viewpoint images by the corresponding image processing section 11.

As a specific example, if the following of the viewpoint image acquired by the imaging section 21a is focused, the video signal transmission frame including the viewpoint image is first input to the image processing section 11a1.

The image processing section 11a1 performs image processing on the viewpoint image acquired by the imaging section 21a. At this time, the image processing section 11a1 stores the status signal indicating "update status" and "processing content" corresponding to the first step in the video signal transmission frame according to the update status of the viewpoint image and the content of the image processing. Then, the image processing section 11a1 outputs the video signal transmission frame to the image processing section 11a2 positioned at the subsequent stage.

Then, the image processing section 11a2 receives the output from the image processing section 11a1, and further performs image processing on the viewpoint image that has undergone the image processing performed by the image processing section 11a1. At this time, the image processing section 11a2 stores the status signal indicating "update status" and "processing content" corresponding to the second step in a different region from the status signal corresponding to the first step in the video signal transmission frame according to the update status of the viewpoint image and the content of the image processing. Then, the image processing section 11a2 outputs the video signal transmission frame to the image selecting unit 13 positioned at the subsequent stage.

As described above, in the image processing apparatus 50 according to the second modified example, the status signal indicating "update status" and "processing content" is stored in the video signal transmission frame in each step of image processing performed on the viewpoint image. Thus, even when an abnormality occurs in any one of the image processing sections 11 corresponding to each step, the control unit 130 of the image selecting unit 13 can individually recognize the statuses of the image processing sections 11 based on the status signals corresponding to the respective steps.

As a result, in the image processing apparatus 50 according to the second modified example, the control unit 130 can feed information back to the corresponding image processing section 11 so that the image processing unit in each of the image processing sections 11 is switched for each step of image processing.

As a specific example, it is assumed that an abnormality occurs in the high function processing unit 112 in the image processing section 11a1 corresponding to the first step, and switching to the low function processing unit 111 is performed.

In this case, information indicating a process performed by the low function processing unit 111 is stored in the video signal transmission frame for transmitting the viewpoint image acquired by the imaging section 21a as the status signal indicating the process content of the image processing of the first step. As a result, the control unit 130 recognizes that the image processing unit in the image processing section 11a1 has been switched to the low function processing unit 111.

Then, the control unit 130 feeds information back to the image processing section 11b1 so that the image processing unit is switched to the low function processing unit 111 in the image processing section 11b1 that performs the image processing of the first step on the viewpoint image acquired by the imaging section 21b.

Through the above operation, control is performed such that the outputs of the image processing section 11a1 and 11b1 that perform the image processing of the first step match the viewpoint images acquired by the imaging sections 21a and 21b.

It is needless to say that the configuration of the image processing apparatus 50, the information transmission method between the components, and the main body of various kinds of controls are not particularly limited as long as the functions of the image processing apparatus 50 according to the second modified example can be implemented.

The example of the configuration of the image processing apparatus configured to be able to switch the image processing unit in each step when the image processing on the viewpoint images acquired by the imaging unit is executed in a plurality of steps has been described above with reference to FIGS. 10 and 11 as the second modified example.

<3. Hardware Configuration>

Figure 12:
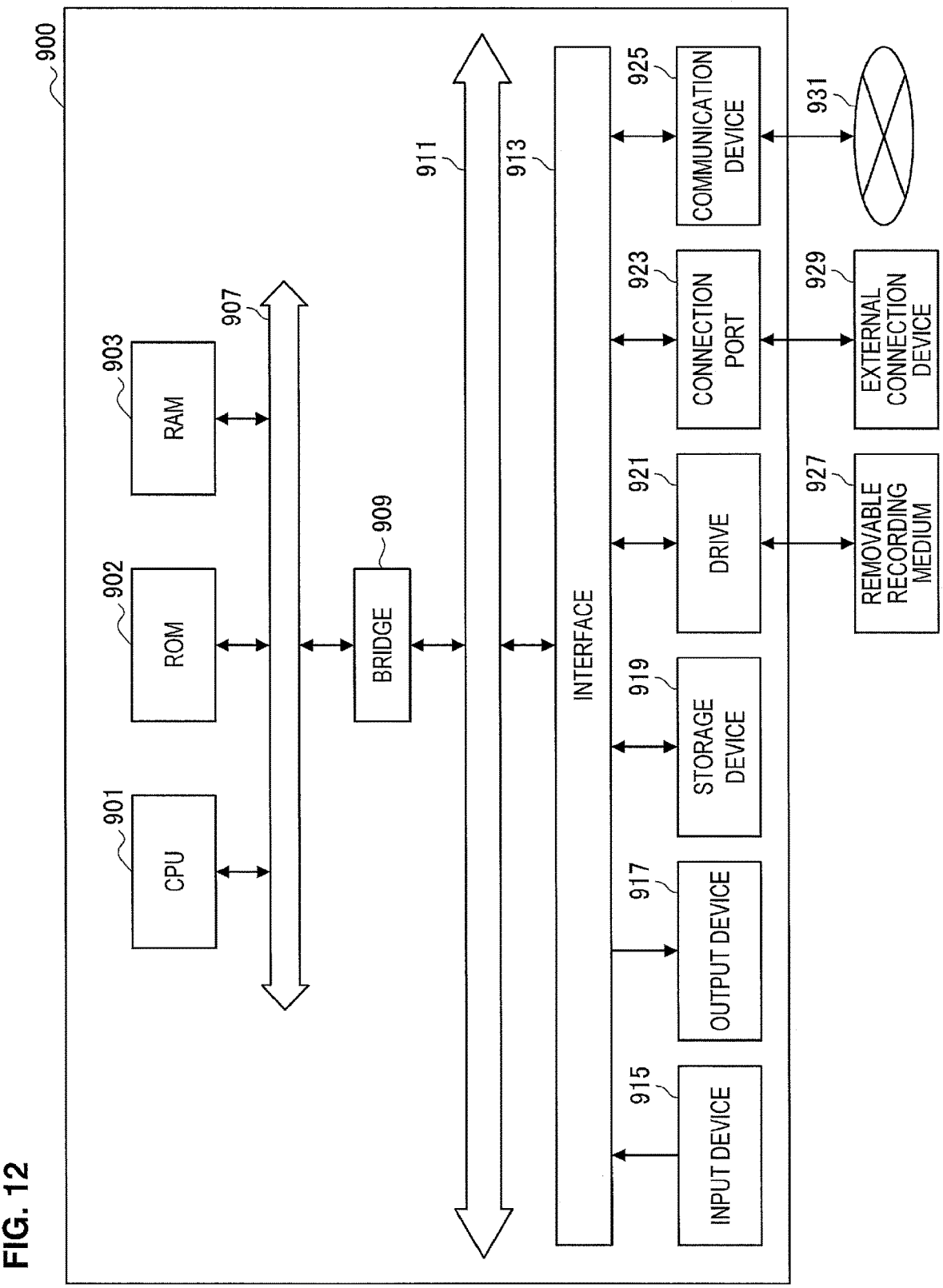
FIG. 12 is a functional block diagram illustrating an exemplary configuration of a hardware configuration of an information processing apparatus configuring a medical stereoscopic observation system according to an embodiment of the present disclosure.

Next, a hardware configuration of an information processing apparatus 900 configuring the medical stereoscopic observation system according to the present embodiment such as the operation video microscope apparatus or the image processing apparatus will be described in detail with reference to FIG. 12. FIG. 12 is a functional block diagram illustrating an exemplary configuration of a hardware configuration of the information processing apparatus 900 configuring the medical stereoscopic observation system according to an embodiment of the present disclosure.

The information processing apparatus 900 configuring the medical stereoscopic observation system according to the present embodiment mainly includes a CPU 901, a ROM 903, and a RAM 905. The information processing apparatus 900 further includes a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls all or some operations of the information processing apparatus 900 according to various kinds of programs recorded in the ROM 903, the RAM 905, the storage device 919, or a removable recording medium 927. The ROM 903 stores a program, an operation parameter, or the like used by the CPU 901. The RAM 905 primarily stores a program used by the CPU 901, a parameter that appropriately changes in execution of a program, or the like. The above-mentioned components are connected with one another by the host bus 907 configured with an internal bus such as a CPU bus. The control unit 110 of each image processing section 11 and the control unit 130 of the image selecting unit 13 described above with reference to FIGS. 4 and 10 may be implemented by the CPU 901.

The host bus 907 is connected to the external bus 911 such as a peripheral component interconnect/interface (PCI) bus through the bridge 909. Further, the input device 915, the output device 917, the storage device 919, the drive 921, the connection port 923, and the communication device 925 are connected to the external bus 911 via the interface 913.

The input device 915 is an operating unit used by the user such as a mouse, a keyboard, a touch panel, a button, a switch, a lever, or a pedal. For example, the input device 915 may be a remote control unit (a so-called remote controller) using infrared light or any other radio waves, and may be an external connection device 929 such as a mobile telephone or a PDA corresponding to an operation of the information processing apparatus 900. Further, for example, the input device 915 is configured with an input control circuit that generates an input signal based on information input by the user using the operating unit, and outputs the input signal to the CPU 901. The user of the information processing apparatus 900 can input various kinds of data to the information processing apparatus 900 or instruct the information processing apparatus 900 to perform a processing operation by operating the input device 915.

The output device 917 is configured with a device capable of visually or acoustically reporting the acquired information to the user. As such a device, there are a display device such as a CRT display device, a liquid crystal display device, a plasma display device, an EL display device or a lamp, an audio output device such as a speaker or a headphone, a printer device, and the like. For example, the output device 917 outputs a result obtained by various kinds of processes performed by the information processing apparatus 900. Specifically, the display device displays a result obtained by various kinds of processes performed by the information processing apparatus 900 in the form of text or an image. Meanwhile, the audio output device converts an audio signal including reproduced audio data, acoustic data, or the like into an analogue signal, and outputs the analogue signal. The reporting unit described above in the first modified example may be implemented by the output device 917.

The storage device 919 is a data storage device configured as an exemplary storage unit of the information processing apparatus 900. For example, the storage device 919 is configured with a magnetic storage device such as a hard disk drive (HDD), a semiconductor storage device, an optical storage device, a magneto optical storage device, or the like. The storage device 919 stores a program executed by the CPU 901, various kinds of data, and the like.

The drive 921 is a recording medium reader/writer, and is equipped in or attached to the information processing apparatus 900. The drive 921 reads information recorded in the removable recording medium 927 mounted thereon such as a magnetic disk, an optical disc, a magneto optical disc, or a semiconductor memory, and outputs the read information to the RAM 905. Further, the drive 921 can write a record in the removable recording medium 927 mounted thereon such as a magnetic disk, an optical disk, a magneto optical disk, or a semiconductor memory. For example, the removable recording medium 927 is a DVD medium, an HD-DVD medium, a Blu-ray (a registered trademark) medium, or the like. Further, the removable recording medium 927 may be a Compact Flash (CF) (a registered trademark), a flash memory, a Secure Digital (SD) memory card, or the like. Furthermore, for example, the removable recording medium 927 may be an integrated circuit (IC) card equipped with a non-contact type IC chip, an electronic device, or the like.

The connection port 923 is a port for connecting a device directly with the information processing apparatus 900. As an example of the connection port 923, there are a Universal Serial Bus (USB) port, an IEEE1394 port, a Small Computer System Interface (SCSI) port, and the like. As another example of the connection port 923, there are an RS-232C port, an optical audio terminal, a High-Definition Multimedia Interface (HDMI) (a registered trademark), and the like. As the external connection device 929 is connected to the connection port 923, the information processing apparatus 900 acquire various kinds of data directly from the external connection device 929 or provide various kinds of data to the external connection device 929.

For example, the communication device 925 is a communication interface configured with a communication device used for a connection with a communication network (network) 931. For example, the communication device 925 is a communication card for a wired or wireless local area network (LAN), Bluetooth (a registered trademark), or wireless USB (WUSB). Further, the communication device 925 may be an optical communication router, an asymmetric digital subscriber line (ADSL) router, various kinds of communication modems, or the like. For example, the communication device 925 can transmit or receive a signal to or from the Internet or another communication device, for example, according to a certain protocol such as TCP/IP. Further, the communication network 931 connected to the communication device 925 is configured with a network connected in a wired or wireless manner, and may be, for example, the Internet, a domestic LAN, infrared ray communication, radio wave communication, satellite communication, or the like.

The example of the hardware configuration capable of implementing the functions of the information processing apparatus 900 configuring the medical stereoscopic observation system according to an embodiment of the present disclosure has been described above. Each component may be configured using a general-purpose member or may be configured with hardware specific to the function of each component. Thus, a hardware configuration to be used can be appropriately changed according to a technical level when the present embodiment is implemented. Although not illustrated in FIG. 12, various kinds of components corresponding to the information processing apparatus 900 (that is, the operation video microscope apparatus or the image processing apparatus) configuring the medical stereoscopic observation system are definitely equipped.

Further, it is possible to create a computer program for implementing the functions of the information processing apparatus 900 configuring the medical stereoscopic observation system according to the present embodiment and install the computer program in a personal computer or the like. Furthermore, it is possible to provide a computer readable recording medium storing the computer program as well. Examples of the recording medium include a magnetic disk, an optical disc, a magneto optical disc, and a flash memory. Further, for example, the computer program may be delivered via a network without using the recording medium.

<4. Conclusion>

As described above, in the medical stereoscopic observation system according to an embodiment of the present disclosure, the status signal indicating the update status of the viewpoint image and the process content of the image processing performed on the viewpoint image is stored in the video signal transmission frame including the viewpoint image through the imaging section 21 or the image processing section 11. The image selecting unit 13 positioned at the stage subsequent to each image processing section 11 monitors the status signal in the video signal transmission frame output from each image processing section 11. Thus, the image selecting unit 13 can recognize the status of the image processing on each viewpoint image by each image processing section 11, that is, the update status of the viewpoint image output from the image processing section 11 and the content of the image processing performed on the viewpoint image based on the monitoring result.

Then, the image selecting unit 13 switches the viewpoint image output as the left eye image and the right eye image according to the recognized status of each image processing section 11. Further, the image selecting unit 13 controls the operation of the image processing section 11 by feeding information back to the other image processing section 11 according to the status of one of the image processing sections 11 that perform the image processing on the viewpoint images. Thus, the other image processing section 11 can recognize the status of one image processing section 11 based on the information fed back from the image selecting unit 13 and switch the output according to the recognized status.

Through this configuration, in the medical stereoscopic observation system according to the present embodiment, even when an abnormality occurs in one of the image processing units that perform the image processing on a plurality of viewpoint images, control can be performed such that the viewpoint image to be observed matches each of the left and right eyes.

The above description has been made in connection with the example in which the status signal is stored in the video signal transmission frame, and the status of the image processing on the viewpoint images is transmitted from the image processing section 11 to the image selecting unit 13 positioned at the subsequent stage. However, it is needless to say that the method is not particularly limited as long as the status signal can be transmitted from the image processing section 11 to the image selecting unit 13. As a specific example, each viewpoint image and the status signal may be individually transmitted as different information. As another example, the status signal may be transmitted through a different path from a path in which the viewpoint image is transmitted.

The above description has been made in connection with the example in which the operation video microscope apparatus with the arm is described as the example of the medical stereoscopic observation apparatus according to an embodiment of the present disclosure, but the medical stereoscopic observation apparatus according to the present embodiment is not necessarily limited to the same configuration. As a specific example, the medical stereoscopic observation apparatus according to the present embodiment may be configured as an operation video microscope apparatus including no arm. In other words, the configuration of the medical stereoscopic observation apparatus according to the present embodiment is not particularly limited as long as an implementation can be made based on the functional configuration illustrated in FIG. 3.

It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative and demonstrative, and not limitative. In other words, the technology according to an embodiment of the present disclosure can exhibit other effects that are evident to those skilled in the art along with or instead of the effects based on the present specification.

Additionally, the present technology may also be configured as below.

(1) A medical stereoscopic observation apparatus, including:
an acquiring unit configured to acquire a status signal according to a status of image processing from each of image processing sections of a plurality of systems that perform the image processing on input image data through a selected image processing unit among a plurality of image processing units and generate output image data to be output as a right eye image or a left eye image; and
a control unit configured to cause a second image processing section different from a first image processing section to switch the selected image processing unit according to the status signal acquired from the first image processing section among the image processing sections of the plurality of systems.

(2) The medical stereoscopic observation apparatus according to (1),
wherein the status signal includes information according to content of the image processing performed by the selected image processing unit, and
wherein the control unit causes the second image processing section to switch the selected image processing unit to the image processing unit according to content of the image processing included in the status signal acquired from the first image processing section.

(3) The medical stereoscopic observation apparatus according to (1),
wherein the status signal includes information according to an update status of the output image data, and
wherein the control unit controls a switching unit that switches the output image data to be output as the right eye image and the left eye image among the output image data output from the image processing section of the plurality of systems according to the update status included in the status signal acquired from each of the image processing sections of the plurality of systems.

(4) The medical stereoscopic observation apparatus according to (3),
wherein the control unit controls the switching unit according to the update status included in the status signal acquired from the first image processing section so that the output image data output from the second image processing section is output as the right eye image and the left eye image.

(5) The medical stereoscopic observation apparatus according to any one of (1) to (4),
wherein the acquiring unit acquires the status signals embedded in the output image data output from the image processing sections.

(6) The medical stereoscopic observation apparatus according to any one of (1) to (5),
wherein each of the image processing sections of the plurality of systems divides a series of image processing on the input image data into a plurality of steps and performs the image processing corresponding to the step through the selected image processing unit among the plurality of image processing units installed for each step,
wherein the acquiring unit acquires the status signal according to the status of the image processing corresponding to each of the plurality of steps, and
wherein the control unit causes the second image processing section to switch, according to the status of the image processing of each step indicated by the status signal acquired from the first image processing section, the selected image processing unit corresponding to the step.

(7) The medical stereoscopic observation apparatus according to any one of (1) to (6),
wherein, when switching of the selected image processing unit is detected in at least any one of the image processing sections of the plurality of systems based on the status signal, the control unit causes a certain reporting unit to report report information indicating the switching.

(8) The medical stereoscopic observation apparatus according to any one of (1) to (7), further including:
the image processing sections of the plurality of systems.

(9) The medical stereoscopic observation apparatus according to (8),
wherein, when a certain image processing unit is selected among the plurality of image processing units, the image processing section presents certain report information in the output image data.

(10) The medical stereoscopic observation apparatus according to (8) or (9),
wherein the image processing section monitors the status of the image processing by the selected image processing unit, switches the image processing unit to another image processing unit according to a monitoring result, and outputs the status signal according to the switching.

(11) The medical stereoscopic observation apparatus according to any one of (1) to (10),
wherein the plurality of image processing units perform different image processing on the input image data.

(12) A medical stereoscopic observation method, including:
acquiring a status signal according to a status of image processing from each of image processing sections of a plurality of systems that perform the image processing on input image data through a selected image processing unit among a plurality of image processing units and generate output image data to be output as a right eye image or a left eye image; and
causing a second image processing section different from a first image processing section to switch the selected image processing unit according to the status signal acquired from the first image processing section among the image processing sections of the plurality of systems through a processor.

(13) A program causing a computer to execute:
acquiring a status signal according to a status of image processing from each of image processing sections of a plurality of systems that perform the image processing on input image data through a selected image processing unit among a plurality of image processing units and generate output image data to be output as a right eye image or a left eye image; and causing a second image processing section different from a first image processing section to switch the selected image processing unit according to the status signal acquired from the first image processing section among the image processing sections of the plurality of systems.

What is claimed is:

1. A medical stereoscopic observation apparatus, comprising:
    circuitry configured to
    acquire a status signal indicating a status of image processing of a first image processing circuit of a plurality of image processing circuits that perform the image processing on input image data, the image processing being performed through a selected image processing unit of a plurality of image processing units of the first image processing circuit, each of the plurality of image processing units being configured to perform different image processing, wherein the first image processing circuit generates output image data, including the status signal inserted in a video signal transmission frame, to be output as a right eye image or a left eye image, and
    cause a second image processing circuit different from the first image processing circuit to switch, based upon the acquired status signal, an initial image processing unit of the second image processing circuit to a different image processing unit of the second image processing circuit such that image processing of the different image processing unit of the second image processing circuit matches the image processing of the selected image processing unit of the first image processing circuit, the second image processing circuit generating output image data to be output as the right eye image or the left eye image,
    wherein matching the image processing of the second image processing circuit to the image processing of the first image processing circuit matches a functional capability between the different image processing unit of the second image processing circuit and the selected image processing unit of the first image processing circuit in order to match a quality of a viewpoint image output between the right eye image and the left eye image.

2. The medical stereoscopic observation apparatus according to claim 1,
    wherein the status signal includes information according to content of the image processing performed by the selected image processing unit of the first image processing circuit, and
    wherein the circuitry is further configured to cause the second image processing circuit to switch the initial image processing unit of the second image processing circuit to the different image processing unit of the second image processing circuit according to content of the image processing included in the status signal acquired from the first image processing circuit.

3. The medical stereoscopic observation apparatus according to claim 1,
    wherein the status signal includes information according to an update status of the output image data of the first image processing circuit, and
    wherein the circuitry is further configured to control a switch that switches the output image data to be output as the right eye image and the left eye image among the output image data output from each one of the plurality of image processing circuits according to the update status included in the status signal acquired from each one of the plurality of image processing circuits.

4. The medical stereoscopic observation apparatus according to claim 3,
    wherein the circuitry is further configured to control the switch according to the update status included in the status signal acquired from the first image processing circuit so that the output image data output from the second image processing circuit is output as the right eye image and the left eye image.

5. The medical stereoscopic observation apparatus according to claim 1,
    wherein the circuitry is further configured to acquire status signals embedded in output image data output from a respective image processing circuit.

6. The medical stereoscopic observation apparatus according to claim 1,
    wherein each one of the plurality of image processing circuits divides a series of image processing on the input image data into a plurality of steps and performs the image processing corresponding to a respective step through a selected image processing unit of the plurality of image processing units installed for each step,
    wherein the circuitry is further configured to acquire the status signal according to the status of the image processing corresponding to each of the plurality of steps, and
    wherein the circuitry is further configured to cause the second image processing circuit to switch, according to the status of the image processing of each step indicated by the status signal acquired from the first image processing circuit, the selected image processing unit corresponding to the step.

7. The medical stereoscopic observation apparatus according to claim 1,
    wherein, when switching of an initial image processing unit, based on the status signal, is detected in an image processing circuit, the circuitry is further configured to cause a report of information indicating the switching.

8. The medical stereoscopic observation apparatus according to claim 1, further comprising:
    each image processing circuit of the plurality of image processing circuits.

9. The medical stereoscopic observation apparatus according to claim 8,
    wherein, in response to a certain image processing unit of an image processing circuit being selected from the plurality of image processing units, the image processing circuit presents certain report information in the output image data.

10. The medical stereoscopic observation apparatus according to claim 8,
    wherein each image processing circuit monitors the status of the image processing by the selected image processing unit, switches the image processing unit to a different image processing unit according to a monitoring result, and outputs the status signal according to the switching.

11. A medical stereoscopic observation method, comprising:
acquiring, by circuitry, a status signal indicating a status of image processing of a first image processing circuit of a plurality of image processing circuits that perform the image processing on input image data, the image processing being performed through a selected image processing unit of a plurality of image processing units of the first image processing circuit, each of the plurality of image processing units being configured to perform different image processing, wherein the first image processing circuit generates output image data, including the status signal inserted in a video signal transmission frame, to be output as a right eye image or a left eye image; and
causing, by the circuitry, a second image processing circuit different from the first image processing circuit to switch, based upon the acquired status signal, an initial image processing unit of the second image processing circuit to a different image processing unit of the second image processing circuit such that image processing of the different image processing unit of the second image processing circuit matches the image processing of the selected image processing unit of the first image processing circuit, the second image processing circuit generating output image data to be output as the right eye image or the left eye image,
wherein matching the image processing of the second image processing circuit to the image processing of the first image processing circuit matches a functional capability between the different image processing unit of the second image processing circuit and the selected image processing unit of the first image processing circuit in order to match a quality of a viewpoint image output between the right eye image and the left eye image.

12. A non-transitory computer readable medium having stored thereon a program that when executed by a computer causes the computer to execute a method comprising:
acquiring a status signal indicating a status of image processing of a first image processing circuit of a plurality of image processing circuits that perform the image processing on input image data, the image processing being performed through a selected image processing unit of a plurality of image processing units of the first image processing circuit, each of the plurality of image processing units being configured to perform different image processing, wherein the first image processing circuit generates output image data, including the status signal inserted in a video signal transmission frame, to be output as a right eye image or a left eye image; and
causing a second image processing circuit different from the first image processing circuit to switch, based upon the acquired status signal, an initial image processing unit to a different image processing unit of the second image processing circuit such that image processing of the different image processing unit of the second image processing circuit matches the image processing of the selected image processing unit of the first image processing circuit, the second image processing circuit generating out image data to be output as the right eye image or the left eye image,
wherein matching the image processing of the second image processing circuit to the image processing of the first image processing circuit matches a functional capability between the different image processing unit of the second image processing circuit and the selected image processing unit of the first image processing circuit in order to match quality of a viewpoint image output between the right eye image and the left eye image.

13. The medical stereoscopic observation apparatus according to claim 1, wherein the functional capability includes a low functional capability and a high functional capability, the low functional capability being associated with outputting an image, and the high functional capability being associated with manipulating the image.

* * * * *